US012648932B2

(12) United States Patent
Nunes Martínez et al.

(10) Patent No.: US 12,648,932 B2
(45) Date of Patent: Jun. 9, 2026

(54) ERGOTHIONEINE, S-METHYL-ERGOTHIONEINE, AND USES THEREOF

(71) Applicants: FUNDACIÓ INSTITUT D'INVESTIGACIÓ BIOMÈDICA DE BELLVITGE (IDIBELL), L'Hospitalet de Llobregat (ES); UNIVERSITAT DE BARCELONA, Barcelona (ES); CONSORCIO CENTRO DE INVESTIGACIÓN BIOMÉDICA EN RED, M.P., Madrid (ES)

(72) Inventors: Virginia Nunes Martínez, L'Hospitalet de Llobregat (ES); Miguel Lopez De Heredia Alonso, L'Hospitalet de Llobregat (ES)

(73) Assignees: FUNDACIÓ INSTITUT D'INVESTIGACIÓ BIOMÈDICA DE BELLVITGE (IDIBELL), L'Hospitalet de Llobregat (ES); UNIVERSITAT DE BARCELONA, Barcelona (ES); CONSORCIO CENTRO DE INVESTIGACIÓN BIOMÉDICA EN RED, M.P., Madrid (ES)

( * ) Notice: Subject to any disclaimer, the term of this patent is extended or adjusted under 35 U.S.C. 154(b) by 1004 days.

(21) Appl. No.: 17/629,530

(22) PCT Filed: Jul. 24, 2020

(86) PCT No.: PCT/EP2020/070964

§ 371 (c)(1),
(2) Date: Jan. 24, 2022

(87) PCT Pub. No.: WO2021/018774

PCT Pub. Date: Feb. 4, 2021

(65) Prior Publication Data

US 2022/0265611 A1 Aug. 25, 2022

(30) Foreign Application Priority Data

Jul. 26, 2019 (EP) .................................... 19382644

(51) Int. Cl.
*A61K 31/4172* (2006.01)
*A61K 31/16* (2006.01)
(Continued)

(52) U.S. Cl.
CPC .......... *A61K 31/4172* (2013.01); *A61K 31/16* (2013.01); *A61K 31/223* (2013.01);
(Continued)

(58) Field of Classification Search
CPC ................ A61K 31/4172; A61P 13/04; G01N 2800/345
See application file for complete search history.

(56) References Cited

U.S. PATENT DOCUMENTS 5,266,595 A 11/1993 Baba

FOREIGN PATENT DOCUMENTS

CA 3122246 A1 6/2020
EP 3410445 A1 12/2012
(Continued)

OTHER PUBLICATIONS

WebMD. (Accessed Jan. 31, 2025). Alpha-lipoic acid: Overview, uses, side effects, precautions, interactions, dosing and reviews. WebMD. https://www.webmd.com/vitamins/ai/ingredientmono-767/alpha-lipoic-acid (Year: 2025).*
(Continued)

*Primary Examiner* — Andrew D Kosar
*Assistant Examiner* — John D Mcanany
(74) *Attorney, Agent, or Firm* — WCF IP

(57) ABSTRACT

The present invention provides S-methyl-L-ergothioneine for use in diagnosis and/or prognosis. The invention also
(Continued)

provides a method for the diagnosis and/or prognosis of a renal disease comprising the step of determining the amount of S-methyl-L-ergothioneine in an isolated test sample of a subject, and methods for deciding or recommending whether to initiate a therapeutic intervention or for determining the efficacy of a therapeutic intervention. It is also herein provided ergothioneine for use in the treatment and/or prevention of a renal lithiasis or an aminoaciduria, and ergothioneine for use in combination therapy.

6 Claims, 17 Drawing Sheets

Specification includes a Sequence Listing.

(51) Int. Cl.
*A61K 31/223* (2006.01)
*A61P 13/04* (2006.01)
*G01N 33/68* (2006.01)

(52) U.S. Cl.
CPC .......... *A61P 13/04* (2018.01); *G01N 33/6815* (2013.01); *G01N 33/6893* (2013.01); *G01N 2800/345* (2013.01)

(56) References Cited

FOREIGN PATENT DOCUMENTS

| | | | |
|---|---|---|---|
| WO | 2010078319 | A1 | 7/2010 |
| WO | 2014186311 | A1 | 11/2014 |

OTHER PUBLICATIONS

Irwin K. Cheah et al, “Administration of Pure Ergothioneine to Healthy Human Subjects: Uptake, Metabolism, and Effects on Biomarkers of Oxidative Damage and Inflammation”, Antioxidants and Redox Signaling, vol. 26, No. 5, Feb. 10, 2017 (Feb. 10, 2017), p. 193-206.

137 Renal Hypouricemia: An Uncommon Cause of Exercise-Induced Renal Failure ED—Collins Allan J; Chan Christopher T, American Journal of Kidney Diseases, vol. 69, No. 4, Apr. 2017 (Apr. 2017).

Tiffany Zee et al, “[alpha]-Lipoic acid treatment prevents cystine urolithiasis in a mouse model of cystinuria”, Nature Medicine, vol. 23, No. 3, Feb. 6, 2017 (Feb. 6, 2017), pp. 288-290.

Teruo Kitagawa, “Classification of Aminoaciduria”, Medicina vol. 21 No. 12, 1984.

* cited by examiner

ERGOTHIONEINE, S-METHYL-ERGOTHIONEINE, AND USES THEREOF

TECHNICAL FIELD

The present invention belongs to the field of medicine. In particular, it belongs to the field of renal disease. The invention herein provided is particularly useful for the diagnosis and treatment of cystine lithiasis.

BACKGROUND ART

Cystinuria is a disease with an autosomal recessive inheritance pattern, characterized by problems in the renal reabsorption and intestinal absorption of cystine and dibasic amino acids, caused by defects in the amino acid transporter rBAT/$b^{0,+}$AT. Cystinuria progresses to cystine lithiasis, which is caused by cystine precipitates in the urinary system that form calculi. These calculi can cause obstruction, infection and, ultimately, renal failure.

Two genes responsible for cystinuria have been identified so far, SLC3A1 and SLC7A9, which encode the rBAT/$b^{0,+}$ AT heteromeric complex, responsible for the $b^{0,+}$ amino acid transport system. This is the main apical reabsorption system for cystine in the kidney. This transporter belongs to the heteromeric amino acid transporter (HAT) family, which is formed by a heavy subunit (rBAT or 4F2hc) linked by a disulfide bridge to a range of light subunits ($b^{0,+}$AT in the case of rBAT).

Cystinuria is diagnosed by demonstrating selective hyperexcretion of cystine and dibasic amino acids in urine. Hexagonal crystals appear in the urine in 20-25% of cystinuric patients, so the only proven clinical manifestation of cystinuria is cystine lithiasis. In fact, cystinuria is the cause of up to 10% of all urinary stones in children. More than 80% of cystinuric patients develop their first cystine stone within the first two decades of life, 75% in both kidneys. Most patients suffer from recurrent stone formation throughout their life, with the need for repeated interventions. Currently, there is no way to predict when a cystinuric patient will develop cystine stones. Moreover, the only way to detect whether the patient has already formed stones is through complex imaging techniques such as KUB X-rays, computerized tomography (CT) and ultrasounds.

Human cystinuria is treated by preventing the formation of cystine stones through high fluid intake, a low-salt diet (<2 g NaCl/day), moderate reduction of protein intake (<0.8 g/day), and urine alkalinization to pH values of at least 7.5 (with potassium citrate, or sodium bicarbonate in severe renal insufficiency cases) to maximize cystine solubility. Even with medical management, the long-term outcome is poor due to insufficient efficacy and low patient compliance.

If prophylaxis fails, patients are treated to dissolve or break the calculi. Calculi are removed by surgical nephrolithotomy (large stones), percutaneous nephrolithotripsy, intracorporeal lithotripsy and, in the case of recently formed calculi, by extracorporeal shock wave lithotripsy. These procedures carry the risk of progressive renal function impairment.

The pharmacological approach is based on oral administration of thiol-based agents, like Penicillamine and Tiopronin, which can displace the redox equilibrium between cystine (insoluble) and cysteine (soluble), by forming a soluble complex with cysteine. Although these agents are quite effective, they have multiple side effects that lead to treatment discontinuation and disease relapse (Halperin E C et al., "The use of D-penicillamine in cystinuria: efficacy and untoward reactions", Yale J Biol Med., 1981, vol. 54(6), pp. 439-46).

Therefore, there is a still a need for simple and inexpensive methods to determine the onset of cystine lithiasis in cystinuric patients, and there is also the need for efficient and non-toxic treatments to prevent or delay the formation of cystine stones.

SUMMARY OF INVENTION

The present inventors have developed a novel method for the diagnosis of cystine lithiasis based on the detection of S-methyl-L-ergothioneine (S-met-L-Erg) in urine samples from patients.

As shown in the examples below, the inventors have surprisingly found that the levels in urine of the amino acid derivative S-met-L-ergothioneine can determine with strong statistical power the presence of renal cystine calculi. This was highly unexpectedly because S-met-L-ergothioneine is a metabolite without any known connections to human disease that has never been detected in samples of cystinuric patients. Thus, the inventors have developed a method that, with the simple analysis of a single metabolite in an easily obtainable sample, allows the precise diagnosis of cystine lithiasis in cystinuric patients.

Before the present invention, the presence of cystine stones in cystinuric patients could only be determined by complex imaging techniques. Thus, the clinical management of cystinuric patients consisted of increased fluid intake and urinary alkalinization until the levels of urinary cystine or renal pain indicate the probable onset of a calculi episode. Only then, the presence of cystine stones was determined by imaging techniques such as CT scan or ultrasounds. These techniques require expensive equipment and cannot even distinguish cystine from other stone chemical constituents.

The simplicity and efficiency of the method herein provided allows the routine testing of urolithiasis in cystinuric patients. This remarkable improvement would facilitate the detection of the cystine stones at their very onset, before they generate any symptoms in the patient, thereby reducing patient suffering and allowing treatment optimization.

Thus, in a first aspect, the invention provides S-methyl-L-ergothioneine for use in diagnosis and/or prognosis.

In a second aspect, the invention provides a method for the diagnosis and/or prognosis of a renal disease, the method comprising the step of determining the amount of S-methyl-L-ergothioneine in an isolated test sample of a subject.

As will be illustrated in examples below in a cystinuric animal model, amounts of S-methyl-L-ergothioneine in urine were lower than in control animals (wild type-WT). Thus, S-methyl-L-ergothioneine is a useful tool to decide or recommend initiation of a therapeutic intervention to avoid, prevent or reduce urolithiasis.

In a third aspect, the invention provides a method for deciding or recommending whether to initiate a therapeutic intervention of a subject suspicious of suffering a renal disease, wherein the method comprises the steps of (a) determining the amount of S-methyl-L-ergothioneine in an isolated test sample of the subject; and

- (b1) deciding or recommending to start a therapeutic intervention if the amount of S-methyl-L-ergothioneine is within a reference value range of subjects suffering renal disease; or alternatively,
- (b2) comparing said amount of S-methyl-L-ergothioneine in an isolated test sample of the subject with a reference value, said reference of a subject do not suffering a renal disease; wherein, if the amount of S-methyl-L-ergothioneine measured in step (a) is lower than the reference value, it is indicative that the subject has to start a therapeutic intervention.

In a fourth aspect, the invention provides a method for determining the efficacy of a therapeutic intervention in a subject already diagnosed with a renal disease, the method comprising the steps of (a) measuring the amount of S-methyl-L-ergothioneine in an isolated test sample of the subject prior to the therapeutic intervention; (b) measuring the amount of S-methyl-L-ergothioneine in an isolated biological sample of the subject once the therapeutic intervention has started; and (c) comparing the amount measured in steps (a) and (b), in such a way that if the amount of S-methyl-L-ergothioneine measured in step (b) is higher than the amount of S-methyl-L-ergothioneine measured in step (a), it is indicative that the medical regimen is effective in the treatment of the renal disease; or, alternatively, the method comprising the steps of (i) measuring the amount of S-methyl-L-ergothioneine in an isolated test sample of the subject once the therapeutic intervention has started; and (ii) comparing the amount measured in step (i) with a reference value of the S-methyl-L-ergothioneine, said reference value of a subject not suffering a renal disease, or said reference value being the amount of S-methyl-L-ergothioneine in an isolated test sample of the subject suffering the renal disease at a previous testing moment, wherein, if the amount of S-methyl-L-ergothioneine measured in step (i) is not lower than the reference value, it is indicative that the medical regimen is effective in the treatment of the renal disease.

In a fifth aspect, the invention provides the use of means for determining the amount of S-methyl-L-ergothioneine in a method as defined above.

In a sixth aspect, the invention provides the use of S-methyl-L-ergothioneine as marker for the diagnosis and/or prognosis of a renal disease in an isolated test sample of a subject.

In a further aspect, the invention provides the ratio S-methyl-L-ergothioneine/L-ergothioneine for use in diagnosis and/or prognosis.

The present inventors have also developed a novel treatment for cystine lithiasis. Surprisingly, as shown in the examples below, the inventors found that the administration of ergothioneine (Erg) prevents or delays renal stone appearance in a cystinuric mouse model.

The current pharmacological treatments for cystine lithiasis are based on thiol-based agents that solubilize the cystine stones by breaking the disulfide bonds thereby forming mixed cysteine disulfide compounds that are more soluble in urine. These known drugs present variable degrees of efficacy and strong secondary effects that restrict their use to short periods of time (Halperin E C et al., supra). As a consequence, cystinuric patients present high rates of disease relapse, which can lead to infections and kidney failure.

Unexpectedly, the inventors found that the administration of ergothioneine not only prevents and delays cystine stone formation, but also it does not generate any side effect in cystinuric mice. This would allow treating cystinuric patients chronically, thereby greatly reducing the lithiasis incidence and relapse. Without wishing to be bound by theory, the different mechanism of action of ergothioneine found by the inventors could be responsible for its extraordinary properties. Contrary to the currently used thiol-based agents, ergothioneine does not directly act on cystine stones. It, however, stimulates the synthesis of glutathione, and increase the intracellular levels of cysteine, methionine, γ-glutamyl-cysteine and the intracellular ratio of cysteine/cystine in renal cells and reduces the redox potential of urine.

The remarkable advantages shown by the novel treatment herein provided are clear indicators that it could be used for the prevention or even treatment of cystine calculi in human patients. In fact, as shown in the examples below, ergothioneine reduced by 50% the number of stone-forming mice; and, the remaining 50% that formed stones, did it with a delay of 1 month in relation to non-treated mice, moreover the formed stones growth rate is lower.

In view of the above, the new treatment against cystine lithiasis herein provided constitutes a great advance in the field of medicine, in particular for the treatment of this genetic disorder.

Thus, in a seventh aspect, the present invention provides ergothioneine for use in the treatment and/or prevention of a renal lithiasis or an aminoaciduria.

This aspect can also be formulated as the use of ergothioneine for the manufacture of a medicament for the treatment and/or prevention of a disease selected from a renal lithiasis and an aminoaciduria. This aspect can also be formulated as a method for treating and/or preventing a disease selected from a renal lithiasis and an aminoaciduria, the method comprising administering a therapeutically effective amount of ergothioneine to a subject in need thereof.

The mechanism of action of ergothioneine makes it particularly suitable for complementing the currently used therapies with cystine-solubilizing agents. Their combined use would allow to simultaneously remove formed stones, and to prevent the formation of new ones. Moreover, the administration of ergothioneine could allow reducing the toxicity of current treatments.

Thus, in an eighth aspect, the present invention provides ergothioneine for use in combination therapy with a compound selected from the group consisting of an additional cystine-solubilizing agent, L-cystine dimethyl ester, L-cystine methyl ester, L-cystine diamide, lipoic acid, and a combination thereof in the treatment and/or prevention of a renal lithiasis or an aminoaciduria.

This aspect can also be formulated as the use of ergothioneine for the manufacture of a medicament for use in combination therapy with a compound selected from the group consisting of an additional cystine-solubilizing agent, L-cystine dimethyl ester, L-cystine methyl ester, L-cystine diamide, lipoic acid, and a combination thereof in the treatment and/or prevention of a disease selected from a renal lithiasis and an aminoaciduria. This aspect can also be formulated as a method for treating and/or preventing a disease selected from a renal lithiasis and an aminoaciduria, the method comprising administering a therapeutically effective amount of ergothioneine in combination with a compound selected from the group consisting of an additional cystine-solubilizing agent, L-cystine dimethyl ester, L-cystine methyl ester, L-cystine diamide, lipoic acid, and a combination thereof to a subject in need thereof.

BRIEF DESCRIPTION OF DRAWINGS

(FIG. 8A) Effect on cystine lithiasis onset. The percentage of lithiasic mice during the 6-month treatment and necropsy is shown for L-Erg treated (ERG) and non-treated mice (Control). The y-axis represents the % of cystine stones, and the x-axis represents the time under treatment, in months. (FIG. 8B) Effect on stone growth rate. Stone growth rate was calculated by a linear regression model for each mouse on those stones with more than 2 data points. The y-axis represents the stone growth rate (mg/day). The bar shows the mean±SEM for untreated (C, n=?) and L-Erg treated mice (ERG, n=3). The result of the statistical analysis is shown on the top.

(FIG. 8C) Effect on urine pH. Urine pH was monitored at the end of the treatment period for L-Erg treated (ERG) and non-treated (C) mice. (FIG. 8D) Effect on urine redox potential. Urine ORP was monitored at the end of the treatment period for L-Erg treated (ERG) and non-treated (Control) mice. The result of the statistical analysis is shown on the top. In (FIG. 8C) and (FIG. 8D), the large black dot represents the mean, and the small black dots over and bellow the boxes the outliers.

DETAILED DESCRIPTION OF THE INVENTION

Figure 1:
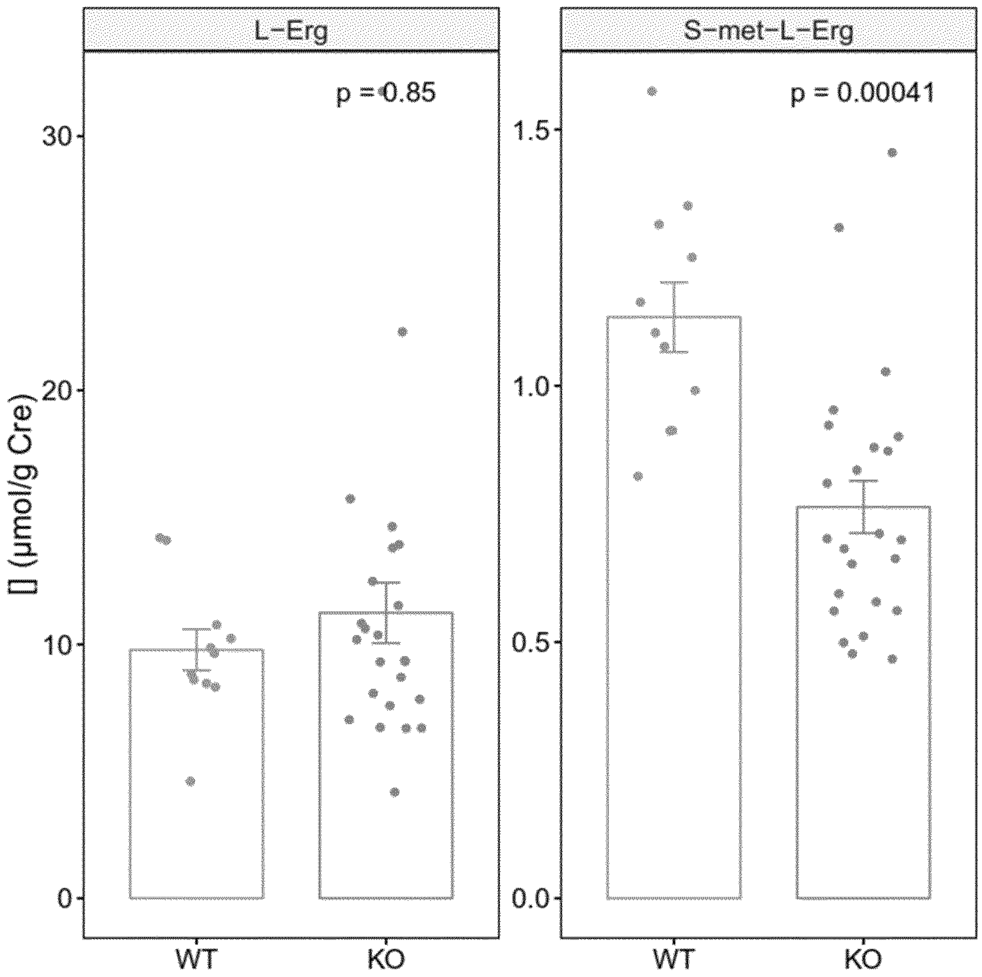
FIG. 1. Determination of L-Erg and S-Met-L-Erg in urine of 6-month-old male mice. L-Erg and S-Met-L-Erg concentration in urine in 6-month-old wt and $Slc7a9^{-/-}$ (KO) male mice. Each dot represents a sample and the bars indicate the mean±SEM. Mann-Whitney probability test value is indicated on the top of each chart.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

As used herein "diagnosis" is understood as becoming aware of a particular medical condition complication or risk in a subject; the determination of the nature of the disease or condition; or the distinguishing of one disease or condition from another. It refers both to the process of attempting to determine or identify the possible disease or disorder, and to the opinion reached by this process. A diagnosis, in the sense of diagnostic procedure, can be regarded as an attempt at classification of an individual's condition into separate and distinct categories that allow medical decisions about treatment and prognosis to be made. Subsequently, a diagnostic opinion is often described in terms of a disease or other condition. However, a diagnosis can take many forms. It might be a matter of detecting the presence and naming the disease, lesion, dysfunction or disability. It might be an exercise to attribute a category for management or for prognosis. It may indicate either degree of abnormality on a continuum or kind of abnormality in a classification.

"Prognosis" as used herein refers to the prediction of the probable progression and outcome of a disease. In the present case, prognosis means, in particular embodiments, differentiation between patients that will develop lithiasis from patients that will not.

In the present invention, the term "reference value" referred to in the methods of the invention is to be understood as a predefined value of S-met-L-erg derived from the amount of said molecular marker in a sample or group of samples. The samples are taken from a subject or group of subjects wherein the presence, absence, stage, histological subtype or grade, or course of the disease has been properly performed previously. This value is used as a threshold to discriminate subjects wherein the condition to be analyzed is present from those wherein such condition is absent. This reference value is also useful for determining whether the subject has to initiate a medical regimen and how effective the regimen is. The subject or subjects from whom the reference value is derived may include subject/s wherein the condition is absent, subject/s wherein the condition is present, or both. The skilled person in the art, making use of the general knowledge, is able to choose the subject or group of subjects more adequate for obtaining the reference value for each of the methods of the present invention. Methods for obtaining the reference value from the group of subjects selected are well-known in the state of the art (Burtis C. A. et al., 2008, Chapter 14, section "Statistical Treatment of Reference Values") In a particular case, "reference value" is a cut-off value defined by means of a conventional ROC analysis (Receiver Operating Characteristic analysis). As the skill person will appreciate, optimal cut-off value will be defined according to the particular applications of the diagnostic or prognostic method: purpose, target population for the diagnosis or prognosis, balance between specificity and sensibility, etc. The term "reference value", as used herein, can be an absolute value; a relative value; a value that has an upper or a lower limit; a range of values; an average value; a median value, a mean value, or a value as compared to a particular control or baseline value.

The levels of a bio marker (in this invention any of L-Erg or S-met-L-erg) are considered to be higher than its reference value when it is at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more higher than the reference value. Likewise, in the context of the present invention, the level of a biomarker is reduced when the level of said biomarker in a sample is lower than a reference value. The levels of a biomarker are considered to be lower than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%: at least 85%, at least 90%, at least 95%, at least 100%, at least 110%, at least 120%, at least 130%, at least 140%, at least 150% or more lower than the reference value.

As used herein, "treatment" is meant to encompass the full or partial relief or restoration of the fitness of a patient. By "therapeutic intervention" refers to the administration of a treatment suitable for the particular disease. In particular embodiments, the therapeutic intervention comprises the administration of ergothioneine.

The term "cystine-solubilizing agent" refers to compounds that have the capacity to increase the solubility of cystine in the urinary tract. In particular, these compounds are thiol-based agents, such as Penicillamine, that break the disulfide bond of cystine and form mixed cysteine disulfide compounds. "Additional cystine solubilizing agent" is meant to include any cystine-solubilizing agent except for ergothioneine.

The expression "pharmaceutical composition" encompasses both compositions intended for human as well as for non-human animals (i.e. veterinarian compositions). In particular, ergothioneine is also useful for the treatment of domestic animals, such as cats and dogs, that are also known to develop cystine lithiasis. The pharmaceutical compositions of the inventions contain a therapeutically effective amount of ergothioneine. The expression "therapeutically effective amount" as used herein, refers to the amount of the compound that, when administered, is sufficient to prevent development of, or alleviate to some extent, one or more of the symptoms of the disease or disorder which is addressed. The particular dose of agent administered according to this invention will of course be determined by the particular circumstances surrounding the case, including the route of administration, the particular condition being treated, and the similar considerations.

The expression "pharmaceutically acceptable carriers or excipient" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of ergothioneine, the pharmaceutically acceptable excipients, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as coloring agents, coating agents, sweetening, and flavoring agents can be present in the composition, according to the judgment of the formulator.

The pharmaceutical compositions containing ergothioneine can be presented in any dosage form, for example, solid or liquid, and can be administered by any suitable route, for example, oral, parenteral, topical, intranasal or sublingual route, for which they will include the pharmaceutically acceptable excipients necessary for the formulation of the desired dosage form.

It is clear for the skilled person that the composition may be prepared using state of the art excipients and applying usual pharmaceutical technologies.

The dosage form may be a solid pharmaceutical composition such as tablets or coated tablets, powders, fine granules, granules, capsules e.g. hard or soft gelatin capsules, troches (pastilles), a bolus and chewable preparations containing ergothioneine.

Alternatively, the pharmaceutical composition may be a semisolid or liquid dosage form such as gel, e.g. a hydrogel, a cream, an ointment, a lotion, water-in-oil or oil-in-water emulsions, suspensions, aerosols, and liquid preparations such as solutions, elixirs, syrups including dry syrups.

The ergothioneine containing pharmaceutical composition of the invention may be administered to a patient in a daily dose in portions over one or several times per day if it is in the dosage form of an orally administered solid preparation such as a tablet or an orally or nasally administered liquid preparation.

In the preparation of the ergothioneine containing composition, a variety of currently used additives may be employed, such as one or more of a filler, a thickening agent, a gelling agent, a binder, a disintegrator, a surfactant, a lubricant, a coating agent, a sustained release agent, a diluent and/or one or more excipients. In addition to the foregoing, the agent of the present invention may, if necessary, further comprise other additives such as a solubilizing agent, a buffering agent, a preservative, an isotonic agent, an emulsifying agent, a suspending agent, a dispersant, a hardening agent, an absorbent, an adhesive, an elasticizing agent, an adsorbent, a perfume, a coloring agent, a corrigent, an antioxidant, a humectant, a light-screening agent, a brightener, a viscosity enhancer, an oil, a tableting adjuvant, and/or an anti-static agent.

More specifically, examples of such additives include one or more excipients such as lactose, corn starch, mannitol, D-sorbitol, crystalline cellulose, erythritol and sucrose; a binder such as hydroxypropyl cellulose (HPC-L), hydroxypropyl methyl cellulose, polyvinyl pyrrolidone, methyl cellulose and gelatinized starch; a disintegrator such as calcium carboxymethyl cellulose, crosslinked sodium carboxymethyl cellulose and crosslinked polyvinyl pyrrolidone (crospovidon); a lubricant such as magnesium stearate and talc; a perfume, for instance, a flavor or an aromatic oil such as apple essence, honey flavour, 1-menthol, vanillin, lemon oil, cinnamon oil, mentha oil or peppermint oil; and/or an adsorbent such as synthetic aluminum silicate and light anhydrous silicic acid.

Moreover, it is also possible to prepare coated pharmaceutical preparations through the use of a currently used coating agent such as hydroxypropyl methyl cellulose, hydroxypropyl cellulose, methyl cellulose or polyvinyl pyrrolidone.

If necessary, a sweetener may likewise be used, such as in troches, syrups and chewable preparations among others. Specific examples of such sweeteners are mannitol, glucose, maltose, starch syrup, malt extract, maltitol, sorbitol, sucrose, unrefined sugar, fructose, lactose, honey, xylitol, hydrangea tea, saccharin, aspartame, cyclamate, Sunett®, aspartyl phenylalanine ester and other malto-oligo saccharides, and oligo saccharides such as maltosyl sucrose, isomaltyrose of reduced type and raffinose, Acesulfame potassium or any kind of sugar alcohols or mixtures thereof such as sorbitol, mannitol and/or xylitol.

As solubilisers any known solubiliser suitable in the medical sector may be used, for example polyethyleneglycols, polyoxyethylene-polyoxypropylene copolymers (e.g. poloxamer 188), glycofurol, arginine, lysine, castor oil, propyleneglycol, solketal, polysorbate, glycerol, polyvinyl pyrrolidone, lecithin, cholesterol, 12-hydroxystearic acid-PEG660-ester, propyleneglycol monostearate, polyoxy-40-hydrogenated castor oil, polyoxyl-10-oleyl-ether, polyoxyl-20-ceto-stearylether and polyoxyl-40-stearate or a mixture thereof.

Any preservatives known for use in the pharmaceutical field may be used, for example, ethanol, benzoic acid and the sodium or potassium salts thereof, sorbic acid and the sodium or potassium salts thereof, chlorobutanol, benzyl alcohol, phenylethanol, methyl-, ethyl-, propyl- or butyl-p-hydroxybenzoates, phenol, m-cresol, p-chloro-m-cresol, those selected from the group of the PHB esters, e.g. mixtures of PHB-methyl with PHB-propylesters, quaternary ammonium compounds such as benzalkonium chloride, thiomersal, phenyl-mercury salts such as nitrates, borates.

The buffer system used to achieve a desired pH value may be, for example, glycine, a mixture of glycine and HCl, a mixture of glycine and sodium hydroxide solution, and the sodium and potassium salts thereof, a mixture of potassium hydrogen phthalate and hydrochloric acid, a mixture of potassium hydrogen phthalate and sodium hydroxide solution or a mixture of glutamic acid and glutamate.

Suitable gelling agents are for example cellulose and its derivatives, like for instance methyl cellulose, carboxymethyl cellulose, hydroxypropylmethyl cellulose, poly(vinyl) alcohol, polyvinylpyrrolidones, polyacrylates, poloxamers, tragacanth, carrageenan, starch and its derivatives or any other gelling agent used in pharmaceutical technology.

Viscosity enhancers which may be mentioned are for example the aforementioned gelling agents in low quantities, glycerol, propylene glycole, polyethylene glycol or polyols, like sorbitol and other sugar alcohols.

The emulsifiers used, apart from the emulsifiers known from the prior art, may include polyoxyethylene derivatives of castor oil or polyoxyethylene alkylethers.

Suitable synthetic or natural, coloring agents known in the pharmaceutical field may be used such as Indigo carmine.

Suitable oily components which may be present are any of the oily substance known from the prior art for the preparation of pharmaceuticals, such as, for example, vegetable oils, in particular, e.g. cotton seed oil, groundnut oil, peanut oil, maize oil, rapeseed oil, sesame oil and soya oil, or triglycerides of moderate chain length, e.g. fractionated coconut oil, or isopropylmyristate, —palmitate or mineral oils or ethyloleate.

The antioxidants used may be any of the antioxidants known from the prior art, for example α-tocopherol, butylhydroxytoluene (BHT) or butylhydroxyanisole (BHA).

Pharmaceutical compositions containing these additives may be prepared according to any method known in this field, depending on the dosage form. It is a matter of course that further additives not explicitly discussed may be used in the formulations used according to the present invention.

As explained above, the present inventors have found for the first time that S-met-L-erg is associated with a medical disease or condition. Thus, the invention provides S-methyl-L-ergothioneine for use in diagnosis and/or prognosis.

S-methyl-L-ergothioneine is a known methyl derivative form of ergothioneine. Ergothioneine has the IUPAC name [1-carboxy-2-(2-sulfanylidene-1,3-dihydroimidazol-4-yl) ethyl]-trimethylazanium, the CAS number 497-30-3, and the formula (I):

(I)

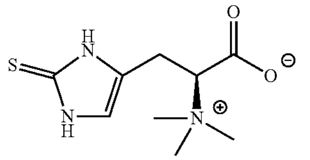

S-methyl-L-ergothioneine has the IUPAC name (2-{S})-3-(2-methylsulfanyl-1-{H}-imidazol-5-yl)-2-(trimethylazaniumyl)propanoate, and the formula (II):

(II)

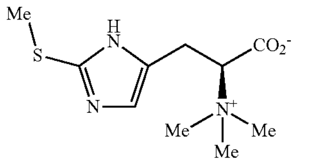

In a particular embodiment, optionally in combination with any of the embodiments provided above or below, the S-methyl-L-ergothioneine is for use in the diagnosis and/or prognosis of a renal disease. In a more particular embodiment, the renal disease is a renal lithiasis or an aminoaciduria. In another particular embodiment, the renal lithiasis is cystine lithiasis. In a more particular embodiment, the aminoaciduria is cystinuria.

As mentioned above, in a second aspect the invention provides a method for the diagnosis or prognosis of a renal disease, the method comprising the step of determining the amount of S-methyl-L-ergothioneine in an isolated test sample of a subject.

In a particular embodiment of the method described above, optionally in combination with any of the embodiments provided above or below, the method further comprises the step of comparing the amount of S-methyl-L-ergothioneine of the subject with a reference value, wherein if the amount determined in the subject is within a range of reference values (reference value) of a subject suffering renal disease, it is indicative that the subject is suspicious of suffering the renal disease; and wherein if the amount is within a range of values of a healthy subject or not suffering any renal disease, in particular not suffering renal lithiasis or an aminoaciduria, it is indicative that the subject is not suspicious of suffering said renal disease.

In a particular embodiment of the method described above, optionally in combination with any of the embodiments provided above or below, the method further comprises the step of comparing the amount of S-methyl-L-ergothioneine of the subject with a reference value, wherein if the amount determined in the subject is different than the reference value, said reference value of a healthy subject or not suffering any renal disease, it is indicative that the subject is suspicious of suffering the renal disease. In a particular embodiment, if the amount determined in the subject is lower than the reference value, said reference value of a subject do not suffering a renal disease, in particular not suffering renal lithiasis or an aminoaciduria, it is indicative that the subject is suspicious of suffering the renal disease. In another more particular embodiment, if the amount determined in the subject is lower than the reference value, it is indicative of bad prognosis.

Figure 5A:
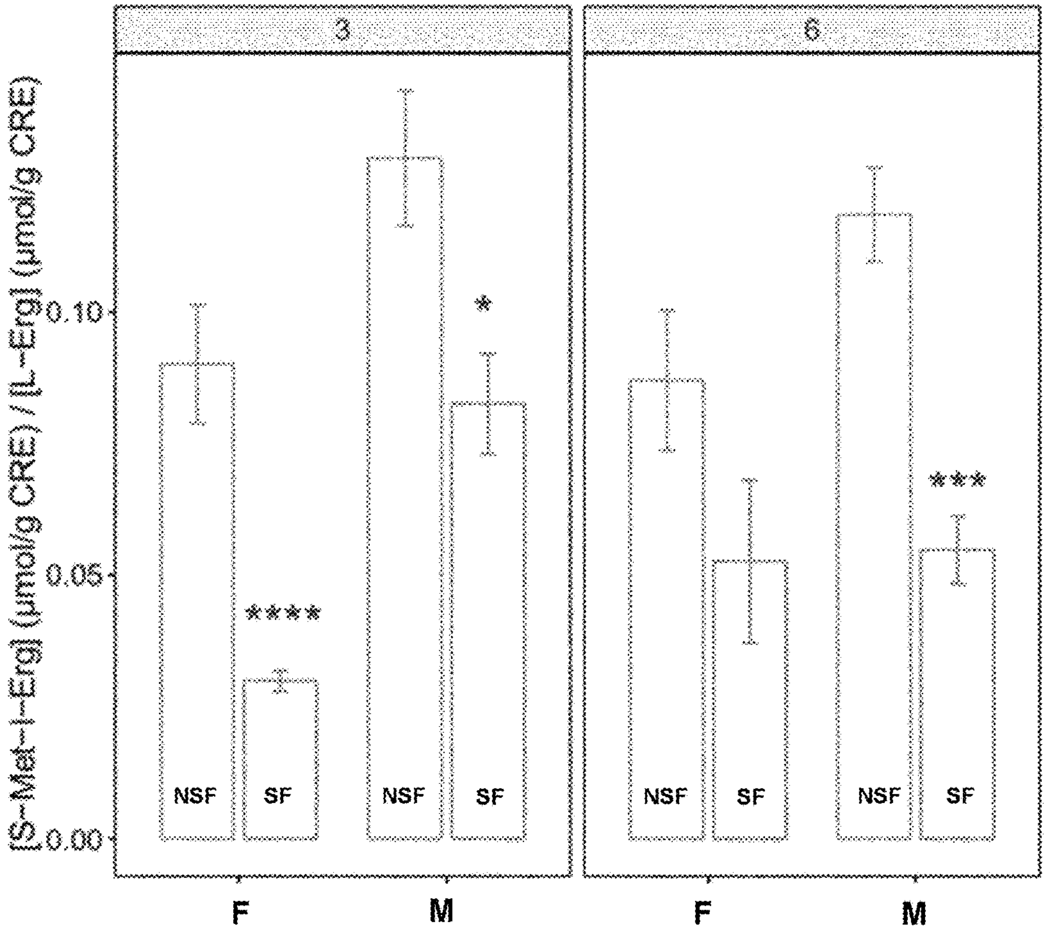
FIG. 5. Urine S-Met-L-Erg/L-Erg ratio in cystinuric mice. A. Urine S-Met-L-Erg/L-Erg ratio in stone former (SF) and non-stone former (NSF) Slc7a9$^{-/-}$ mice. The bars indicate the mean±SEM. Mann-Whitney probability test value is indicated as*, P≤0.05, *, P≤0.001, **, P≤0.0001 vs. non-stone former mice. B. Receiver operator characteristic curve displaying the performance of the Urine S-Met-L-Erg/L-Erg ratio about distinguishing SF from NSF. AUC, Area Under the Curve. The y-axis represents de True positive fraction and the x-axis represents the False positive fraction.
Figure 5B:
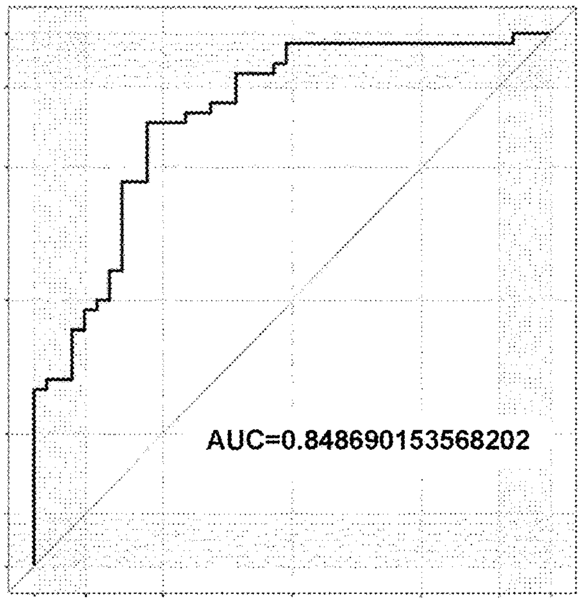

As shown in the examples below, the inventors found that the ratio between the amount of S-methyl-L-ergothioneine and L-ergothioneine in urine samples provided even better statistical results for distinguishing lithiasic from non-lithiasic mice (FIG. 5B). In fact, the S-methyl-L-ergothioneine/L-ergothioneine ratio allowed classifying the mice with a specificity and a sensitivity of 100% using two different analysis methodologies.

Thus, in a particular embodiment of the method described above, optionally in combination with any of the embodiments provided above or below, the method further comprises the step of determining the amount of ergothioneine in the isolated test sample of the subject. In an even more particular embodiment, the method further comprises the steps of determining the amount of ergothioneine in the isolated test sample of the subject and calculating the ratio between the amounts of S-methyl-L-ergothioneine and L-ergothioneine.

In a particular embodiment of the method described above, optionally in combination with any of the embodiments provided above or below, the method further comprises the steps of determining the amount of L-ergothioneine in the isolated test sample of the subject, calculating the ratio between the amounts of S-methyl-L-ergothioneine and L-ergothioneine, and comparing the ratio with a reference value, wherein if the ratio determined in the subject is within a range of reference values (reference value) of a subject suffering renal disease, it is indicative that the subject is suspicious of suffering the said renal disease; and wherein if the ratio is within a range of values of a healthy subject or not suffering any renal disease, in particular not suffering renal lithiasis or an aminoaciduria, it is indicative that the subject is not suspicious of suffering said renal disease.

In a particular embodiment of the method described above, optionally in combination with any of the embodiments provided above or below, the method further comprises the steps of determining the amount of L-ergothioneine in the isolated test sample of the subject, calculating the ratio between the amounts of S-methyl-L-ergothioneine and L-ergothioneine, and comparing the ratio with a reference value, wherein if the ratio determined in the subject is different than the reference value, said reference value of a healthy subject or nor suffering any renal disease, in particular not suffering renal lithiasis or an aminoaciduria, it is indicative that the subject is suspicious of suffering the renal disease. In a more particular embodiment, if the ratio determined in the subject is lower than the said reference value, it is indicative that the subject is suspicious of suffering the renal disease.

S-methyl-L-ergothioneine and L-ergothioneine levels can be determined following routinely techniques in the field of diagnostics. The skill in the art can adjust the parameters of the techniques for optimal results. Thus, in a particular embodiment of the method described above, the amount of S-methyl-L-ergothioneine and/or L-ergothioneine is determined by mass spectrometry, high performance liquid chromatography (HPLC), derivatization, chemodetection, and combinations thereof.

As mentioned before, a further aspect of the invention provides the use of means for determining the amount of S-methyl-L-ergothioneine in a method as defined above.

In a particular embodiment, optionally in combination with any of the embodiments provided above or below, the means form part of a kit.

The term "kit", as used herein, refers to a product containing the different reagents (or reagent means) necessary for carrying out the methods of the invention packed so as to allow their transport and storage. Materials suitable for packing the components of the kit include crystal, plastic (e.g. polyethylene, polypropylene, polycarbonate), bottles, vials, paper, or envelopes.

In a particular embodiment of the invention, the means for determining the amount of S-methyl-L-ergothioneine comprise isotopically labelled S-methyl-L-ergothioneine and/or L-ergothioneine, more in particular deuterated S-methyl-L-ergothioneine and/or L-ergothioneine, and the method is carried out by adding to a test sample, labelled S-methyl-L-ergothioneine and/or labelled L-ergothioneine as spike-in compound or mixture.

In a more particular embodiment, the means comprise a mixture of isotopically labelled S-methyl-L-ergothioneine and isotopically labelled L-ergothioneine.

In this particular embodiment where isotopically labelled S-methyl-L-ergothioneine and/or L-ergothioneine are used, further means are included comprising non-isotopically labelled S-methyl-L-ergothioneine and/or L-ergothioneine, used as positive control means in the method.

Therefore, particular kits for carrying out the method of the invention comprise or consist of a first vial with a composition comprising isotopically labelled S-methyl-L-ergothioneine and/or L-ergothioneine; and a second vial with a composition comprising S-methyl-L-ergothioneine and/or L-ergothioneine. In these kits, the first vial includes the means for spiking into the tested isolated samples, into a standard curve, of for a Quality Control (QC) test. The second vial includes the means to prepare a standard curve. Additionally, the kits of the invention can contain instructions for the simultaneous, sequential or separate use of the different means for determining the amount of S-methyl-L-ergothioneine and/or L-ergothioneine which are in the kit. Said instructions can be in the form of printed material or in the form of an electronic support capable of storing instructions susceptible of being read or understood, such as, for example, electronic storage media (e.g. magnetic disks, tapes), or optical media (e.g. CD-ROM, DVD), or audio materials. Additionally, or alternatively, the media can contain internet addresses that provide said instructions.

As mentioned above, in a further aspect the invention provides the use of S-methyl-L-ergothioneine as marker for the diagnosis and/or prognosis of a renal disease in an isolated test sample of a subject. In a particular embodiment, the S-methyl-L-ergothioneine is used together with L-ergothioneine as marker for the diagnosis and/or prognosis of a renal disease in an isolated test sample of a subject. In a more particular embodiment, the ratio between the amounts of S-methyl-L-ergothioneine and L-ergothioneine is used as marker for the diagnosis and/or prognosis of a renal disease in an isolated test sample of a subject.

In a particular embodiment of the methods and the uses defined above, optionally in combination with any of the embodiments provided above or below, the isolated test sample is selected from serum, plasma, saliva, pleural, cerebral spinal fluid (CSF), blood, amniotic fluid, urine, feces, mucus, cell extracts and pus. In a more particular embodiment, optionally in combination with any of the embodiments provided above or below, the isolated test sample is a urine sample.

In a particular embodiment of the methods and the uses defined above, optionally in combination with any of the embodiments provided above or below, the subject suffers from an aminoaciduria. In a more particular embodiment, the aminoaciduria is cystinuria. As shown in the examples below, the method of the invention is particularly useful for the diagnosis of cystine lithiasis in subjects suffering from cystinuria.

Various species of mammals are known to develop cystine stones in the kidney as a result of conditions that produce anomalous accumulation of cystine in urine. The method of the invention can be applied to all of them. Thus, in another particular embodiment of the methods and the uses defined above, optionally in combination with any of the embodiments provided above or below, the subject is a mammal. In a more particular embodiment, the mammal is a domestic animal mammal. In another particular embodiment, optionally in combination with any of the embodiments provided above or below, the mammal is a human.

In a particular embodiment of the S-methyl-L-ergothioneine for use as disclosed above, the methods and the uses defined above, optionally in combination with any of the embodiments provided above or below, the renal disease is a renal lithiasis or an aminoaciduria. In a more particular embodiment, the renal lithiasis is cystine lithiasis. In another particular embodiment, the aminoaciduria is cystinuria.

Thus, in a particular embodiment, optionally in combination with any of the embodiments provided above or below, the method is for the diagnosis of cystine lithiasis. More in particular, the method is for the diagnosis of cystine lithiasis in a subject suffering from cystinuria. In another particular embodiment, the method is for the prognosis of cystinuria. The method of the invention would be useful for determining the presence of cystine stones and also for predicting the appearance of cystine stones in a subject that suffers from cystinuria.

As mentioned above, it is particularly important to diagnose the urolithiasis as soon as possible in order to provide the adequate treatment and to avoid the complications generated by big kidney stones (i.e. obstructions, infections, and renal failure). The method of the invention allows such timely diagnosis.

All the methods and uses herein provided can be carried out by determining in the isolated test sample the amount of S-methyl-L-ergothioneine, or the amounts of S-methyl-L-ergothioneine and L-ergothioneine and calculating de ratio S-methyl-L-ergothioneine/L-ergothioneine.

Thus, as mentioned above, in a further aspect, the invention provides the ratio S-methyl-L-ergothioneine/L-ergothioneine for use in diagnosis and/or prognosis. All the embodiments above provided are also meant to apply to this further aspect.

Inventors also realized that urine redox potential or redox status (ORP) of a cystinuric mice model not forming cystine stones was lower than urine ORP in mice forming stones. Thus, this parameter is also proposed for the in vitro differential diagnosis or prognosis in cystinuric animals, including humans.

Redox potential (also known as oxidation/reduction potential, ORP) is a measure of the tendency of a chemical species (i.e. isolated samples; urine) to acquire electrons from or lose electrons to an electrode and thereby be reduced or oxidised, respectively. Redox potential is measured in volts (V), or millivolts (mV). Each species has its own intrinsic redox potential; for example, the more positive the reduction potential (reduction potential is more often used due to general formalism in electrochemistry), the greater the species' affinity for electrons and tendency to be reduced.

In a more particular embodiment of any of the methods for the diagnosis or prognosis of a renal disease above disclosed, in particular of renal lithiasis or aminoaciduria, more in particular cystine lithiasis and cystinuria herewith provided, the method further comprises:

(a) determining in an isolated sample of a subject, in particular a urine sample, the redox potential (ORP);
(b) comparing ORP of (a) with a reference value; and
(c) diagnosing the subject as a non-forming stones subject if (c1) ORP is within a reference value range of non-forming stones subjects, or alternatively, if (c2) ORP is lower than a reference vale, said reference obtained from subjects previously classified as forming stones subjects.

The term "non-forming stones subject" means that the subject has a low or null tendency to develop stones in urine due to environmental conditions in said urine, as well as due to any other more complex cause (genetic background, diet, etc.).

Thus, with ORP measure besides determination of S-methyl-L-ergothioneine, or the amounts of S-methyl-L-ergothioneine and L-ergothioneine, additional reliable information on the diagnosis or prognosis of the disease is acquired with the detection of subjects with a higher tendency to form stones. This information is then useful for the recommendation or decision on starting an adequate therapeutic intervention.

The invention also relates to the use of ORP as single diagnostic or prognostic marker of renal disease, more in particular diagnostic or prognostic marker of renal lithiasis or aminoaciduria, even more in particular of cystine lithiasis or cystinuria. Thus, the invention includes an in vitro method for the diagnosis or prognosis of a renal disease comprising determining in an isolated sample of a subject, in particular in urine, the redox potential. In a more particular embodiment of the method, said ORP of the isolated sample is then compared with a reference value to classify the subject as a non-forming stone subject or as a forming stone subject as disclosed above.

The in vitro methods of the invention provide diagnostic and/or prognostic information. In one embodiment, the methods of the invention further comprise the steps of (i) collecting the diagnostic and/or prognostic information, and (ii) saving the information in a data carrier.

In the sense of the invention a "data carrier" is to be understood as any means that contain meaningful information data for the differential diagnosis and/or prognosis of renal lithiasis and an aminoaciduria, such as paper. The carrier may also be any entity or device capable of carrying the prognosis data. For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the diagnosis/prognosis data are embodied in a signal that may be conveyed directly by a cable or other device or means, the carrier may be constituted by such cable or other device or means. Other carriers relate to USB devices and computer archives. Examples of suitable data carrier are paper, CDs, USB, computer archives in PCs, or sound registration with the same information.

The invention also provides a method for treating a patient with a renal lithiasis or an aminoaciduria, in particular cystinuria, the method comprising the steps of:

(a) determining the amount of S-methyl-L-ergothioneine in an isolated test sample of a subject, and optionally the amount of L-ergothioneine and calculating the ratio between the amounts of S-methyl-L-ergothioneine and L-ergothioneine;
(b) comparing the amount or ratio determined in (a) with a reference value; and
(c1) wherein if the level determined in (a) is lower than the reference value, said reference of a subject not suffering renal lithiasis or an aminoaciduria, or alternatively, (c2) wherein if the level determined in (a) is within a reference value range of subjects suffering renal lithiasis or an aminoaciduria, administering a pharmaceutically effective amount of a cystine-solubilizing agent to the subject in need thereof The invention also provides a method for treating a patient with a renal lithiasis or an aminoaciduria, the method comprising the steps of:

(a) determining the amount of S-methyl-L-ergothioneine in an isolated test sample of a subject, and optionally the amount of L-ergothioneine and calculating the ratio between the amounts of S-methyl-L-ergothioneine and L-ergothioneine;
(b) comparing the amount or ratio determined in (a) with a reference value; and
(c1) wherein if the level determined in (a) is lower than the reference value, said reference of a subject not suffering renal lithiasis or an aminoaciduria, or alternatively, (c2) wherein if the level determined in (a) is within a reference value range of subjects suffering renal lithiasis or an aminoaciduria, administering a pharmaceutically effective amount of ergothioneine to the subject in need.

As mentioned before, the inventors have also developed an effective and safe treatment for aminoacidurias and the associated renal lithiasis.

In a particular embodiment of the ergothioneine for use as disclosed above, optionally in combination with any of the embodiments provided above or below, the renal lithiasis is cystine lithiasis.

In another particular embodiment of the ergothioneine for use as disclosed above, optionally in combination with any of the embodiments provided above or below, the aminoaciduria is cystinuria.

In a particular embodiment of the ergothioneine for use as disclosed above, optionally in combination with any of the embodiments provided above or below, the ergothioneine is administered in the form of a pharmaceutical composition together with one or more pharmaceutically acceptable excipients and/or carriers. In a more particular embodiment, the pharmaceutical composition is an oral pharmaceutical composition.

In a particular embodiment, optionally in combination with any of the embodiments provided above or below, the ergothioneine is administered in a dose from 0.01 to 500 mg/kg body weight per day. In a more particular embodiment, in a dose from 0.05 to 300 mg/kg body weight per day. In an even more particular embodiment, in a dose from 0.1 to 200 mg/kg body weight per day.

As mentioned before, the invention also provides ergothioneine for use in combination therapy with a compound selected from the group consisting of an additional cystine-solubilizing agent, L-cystine dimethyl ester, L-cystine methyl ester, L-cystine diamide, lipoic acid, and a combination thereof in the treatment and/or prevention of a renal lithiasis or an aminoaciduria.

All the embodiments of the ergothioneine for use defined above are also meant to apply to the ergothioneine for use in combination therapy.

In a particular embodiment of the ergothioneine for use in combination therapy defined above, optionally in combination with any of the embodiments provided above or below, the additional cystine solubilizing agent is selected from the group comprising Penicillamine, Tiopronin, Captopril, and Bucillamine. In a more particular embodiment, the cystine solubilizing agent is selected from Penicillamine and Tiopronin.

In a particular embodiment of the ergothioneine for use in combination therapy as defined above, the ergothioneine is administered simultaneously, sequentially or separately with a compound selected from the group consisting of an additional cystine-solubilizing agent, L-cystine dimethyl ester, L-cystine methyl ester, L-cystine diamide, lipoic acid, and a combination thereof.

In a particular embodiment of the ergothioneine for use as defined above, optionally in combination with any of the embodiments provided above or below, the ergothioneine is L-ergothioneine.

Thus, in a particular embodiment optionally in combination with any of the embodiments provided allow or below, the invention provides L-ergothioneine for use in the treatment and/or prevention of a renal lithiasis or an aminoaciduria. More particularly, the L-ergothioneine is for use in the treatment and/or prevention of cystine lithiasis or cystinuria.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim and shall not be construed as limiting the scope of the claim. Furthermore, the present invention covers all possible combinations of particular and preferred embodiments described herein.

EXAMPLES

Example 1: Urine Markers of Cystine Lithiasis in a Cystinuria Mouse Model

Methods

Mice Care

All animal protocols were approved by the Animal Experimentation Ethics Committee of IDIBELL (AAALAC accredited facility, B9900010) and by the corresponding Department of Generalitat de Catalunya according to EU directive 2010/63/EU. Experiments were carried out with the highest scientific, humane, and ethical principles. All animals were of pure genetic background C57BL/6J and maintained in a 12 h light-dark cycle in humidity and temperature-controlled room. Animals were housed in sterile cages with free access to food (Teklad Global 14% Protein Diet, Harlan Laboratories) and water.

Knocking Out Slc22a4 in the Type-B Cystinuric Mouse Model (Slc7a9$^{-/-}$)

Single loss-of-function mouse models for Slc7a9$^{-/-}$ (mouse model for cystinuria) and Slc22a4$^{-/-}$ (Feliubadaló et al "Slc7a9-deficient mice develop cystinuria non-I and cystine urolithiasis" Hum Mol Genet 2003; vol 12; pp. 2097-2108; Kato Y. et al., "Gene knockout and metabolome analysis of carnitine/organic cation transporter OCTN1", *Pharm. Res.,* 2010; vol 27, pp. 832-40) were crossed to obtain double heterozygous mice, which were backcrossed to get the 3 expected genotypes, including the double KO Slc7a9$^{-/-}$ Slc22a4$^{-/-}$ (dKO).

For genotyping analyses, genomic DNA was isolated from tail tissue. Slc22a4$^{-/-}$ genotype was confirmed by PCR (30 cycles at 60° C. annealing temperature), based on a 3'-primer strategy (F: 5'-gggtgtggtccagaggact-3', SEQ ID NO: 1; R wt-specific: 5'-tagttgccagccatctgttg-3', SEQ ID NO: 2; R KO-specific: 5'-gactgacataccattgaagc-3', SEQ ID NO: 3) allowing to distinguish genotypes by generating 255 bp and 313 bp fragments from the wt and KO alleles, respectively. For Slc7a9$^{-/-}$, genotype was confirmed by PCR (30 cycles at 60° C. annealing temperature), based on a 3'-primer strategy (F: 5'-gcattcgccacaggctcttc-3', SEQ ID NO: 4; R-wt: 5'-ctgtgttggccagcacagac-3', SEQ ID NO: 5; R KO-specific: 5'-cgcagcgcatcgccttctat-3', SEQ ID NO: 6), allowing to distinguish genotypes by generating 452 bp and 311 bp fragments from the wt and KO alleles, respectively.

Sample Collection

Mice from each genotype were individually housed in metabolic cages for 4 days with the first day as an adaptation period. Mice weight, water and food intake, and feces and urine excreted were monitored daily. 24 h urine samples were collected and kept at −80° C. until further analysis with 50 μL thymol 10% in isopropanol as preservative. Blood was obtained by intracardiac puncture with EDTA coated syringes and transferred into Microvette EDTA-tubes (Sarstedt) and centrifuged at 3000 rpm for 10 min and 4° C. in a minifuge after a 10 min incubation at room temperature. Plasma was then separated into a new tube and kept on ice. Plasma absorbance at 414 nm was then determined to quantify hemolysis with a NanoDrop spectrophotometer and only those with OD<0.2 were considered for the further analysis. Plasma samples were stored at −80° C. and centrifuged erythrocytes (RBCs) were also collected and stored at −80° C.

L-Erq and S-Met-L-Erq Determination in Plasma, Blood and Erythrocytes

L-Erg in plasma and red blood cells was measured as described by Sotgia S. et al. "Plasma L-ergothioneine measurement by high-performance liquid chromatography and capillary electrophoresis after a pre-column derivatization with 5-iodoacetamidofluorescein (5-IAF) and fluorescence detection". Antopolsky M, ed. *PLoS One* 2013; vol. 8: e70374, while plasma creatinine as described by (Zinellu A. et al., "Assay for the simultaneous determination of guanidinoacetic acid, creatinine and creatine in plasma and urine by capillary electrophoresis UV-detection", *J. Sep. Sci.,* 2006).

For plasma ergothioneine measurement, 100 μL of sample were added with 100 μL of acetonitrile and, after vigorous vortex-mixing, centrifuged at 17000×g for 10 min at room temperature. 150 μL of clear supernatant were added with 50 μL of a solution consisting of 5-iodoacetamidofluorescein (770 μmol/L) and sodium phosphate tribasic dodecahydrate (150 mmol/L) at pH 13. After vigorous vortex-mixing, reaction mixture was left in a light-protected area for 30 min at room temperature. Finally, samples were diluted fifty times and analyzed by capillary electrophoresis coupled to a laser-induced fluorescence detector.

For the erythrocyte ergothioneine measurement, a 100 μL-volume of water was added to 100 μL of red blood cells and mixed thoroughly by vigorous vortex-mixing; then 400 μL of acetonitrile were added and thoroughly vortex-mixed for 5 min. After centrifugation at 17000×g for 10 min at room temperature, 2 μL of clear supernatant were analyzed by ultra-performance liquid chromatography coupled to a photodiode array detector set at 262 nm. For plasma creatinine measurement, samples were filtered on microcon-10 devices at 3000×g for 5 min then directly analyzed by capillary electrophoresis coupled to a photodiode array detector set at 190 nm.

Analysis of Compound Concentrations in Urine

Creatinine concentrations in thawed urine samples were determined with Creatinine Assay Kit (Sigma) as indicated by manufacturer after filtering through 10 kDa MWCO spin filters (Amicon Ultra 0.5 mL, Millipore).

For L-Erg and S-met-L-Erg analysis in urine, thawed urine samples where centrifuged at 1000×g 5 min and 4° C. to remove any debris. Then, supernatants where 1/10th diluted in Milli-Q water supplemented with deuterated L-Erg and S-met-L-erg (50 ng/mL final concentration each). The samples where then filtered through eXtremeFV PVDF 0.2 μm filter vials (Thomson Instrument Company), and L-Erg and S-met quantified by UPLC-MS/MS. LC-MS/MS was carried out using a Dionex LPG-3400SD LC System coupled to Thermo LTQ-XL ESI tandem mass spectrometer. Samples were kept at 15° C. in the autosampler. 20 μl of the diluted samples and standards were injected into a ZORBAX Eclipse Plus C18 (3.5 μm, 75×4.6 mm; Agilent) maintained at 35° C. Solvent A was 0.05% formic acid in ultrapure water, and Solvent B was acetonitrile in 0.05% formic acid. Chromatography was carried out at a flow rate of 0.9 ml/min under isocratic conditions (99% A:1% B) for 3 minutes.

Mass spectrometry was carried out under positive ion, electrospray ionization mode, using multiple reaction monitoring (MRM) for quantification of specific target ions. Source voltage was set at 3.0 kV, and capillary temperature was kept at 375° C. Nitrogen sheath gas flow was 90 (au), auxiliary gas flow was 10 (au) and Sweep gas flow was 6 (au). Alphagaz 2 helium (air liquid) was used as collision gas. Precursor to product ion transitions for each compound were as follows: Ergothioneine: 230.0→186.0; d3-Ergothioneine 233.0→189.0; S-methyl-Ergothioneine: 244.0→200.0; d3-S-methyl-Ergothioneine: 247.0→203.0. In all cases, isolation width (m/z) and CID collision energies were 2.0 and 20%, respectively.

Results

Sex and Age Differences in L-Erg Concentration in Blood and Urine

The inventors first analyzed L-Erg content in blood and urine of wt and Slc7a9$^{-/-}$ male mice looking for differences that could be explained by the differential expression. L-Erg concentration in blood, plasma or red blood cells (RBC) showed no significative differences between wt and cystinuric male mice, being the concentrations in plasma and blood higher in Slc7a9$^{-/-}$ male mice and lower in RBC (data not shown). As L-Erg concentration in RBC was two orders of magnitude higher than in plasma and, to account for putative effects of hemolysis in the determination of L-Erg in plasma the contribution of hemolysis to the plasma concentration of L-Erg was analyzed and found no correlation between both variables (data not shown). Urine concentration of L-Erg showed also a non-significant increase in Slc7a9$^{-/-}$ male mice (FIG. 1), but, unexpectedly, the concentration of S-met-L-Erg (a metabolite of L-Erg) showed a significant decrease in Slc7a9$^{-/-}$ male mice (FIG. 1). These results indicate that S-met-L-Erg in urine could be used as a biomarker of cystine lithiasis.

Figure 2:
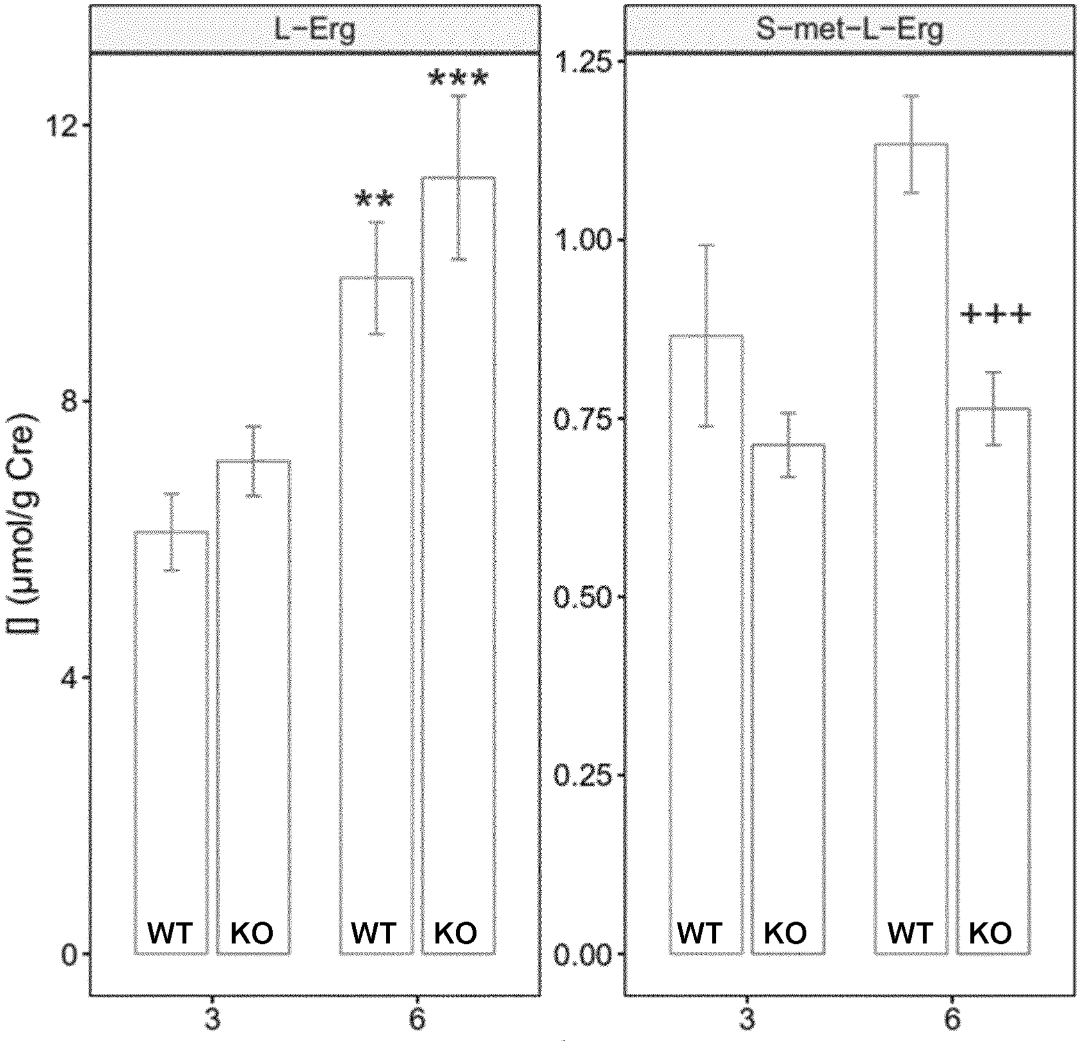
FIG. 2. Differences of L-Erg and S-Met-L-Erg concentration in urine in male mice at different ages. L-Erg and S-Met-L-Erg concentration in urine in 3- and 6-month-old wt and Slc7a9$^{-/-}$ (KO) male mice. The bars indicate the mean±SEM. Mann-Whitney probability test value is indicated as , P≤0.01*, P≤0.001 of 3-vs. 6-month old, and +++, P≤0.001 of wt vs. KO.

Looking for any difference related to age as reported in humans, the inventors, then, investigated if the above described situation is maintained at another age. No differences were detected in L-Erg concentration in blood, plasma or RBC at 3 months of age between wt and cystinuric male mice, but a significant two-fold increase in the L-Erg concentration in RBC was detected for all mice when comparing 6 versus 3 months of age (data not shown). Similarly, L-Erg concentration in urine was also significantly higher at 6-months of age and no differences in the urine concentration of S-Met-L-Erg related to age where detected (FIG. 2).

To check for differences related to sex, the inventors then investigated the concentration of L-Erg in blood and urine and S-Met-L-Erg in urine as above. At 3 months of age, no gender-related differences were seen in L-Erg concentration in blood, plasma or RBC except for a 33% reduction (p=0.093) in L-Erg concentration in RBCs (data not shown). But the urine concentration of S-Met-L-Erg was significatively reduced almost 2-fold in both wt and Slc7a9$^{-/-}$ female mice. Furthermore, a significant decrease in the concentration of this metabolite and a significatively increase in L-Erg were detected in female Slc7a9$^{-/-}$ mice versus female wt mice (data not shown).

Figure 3:
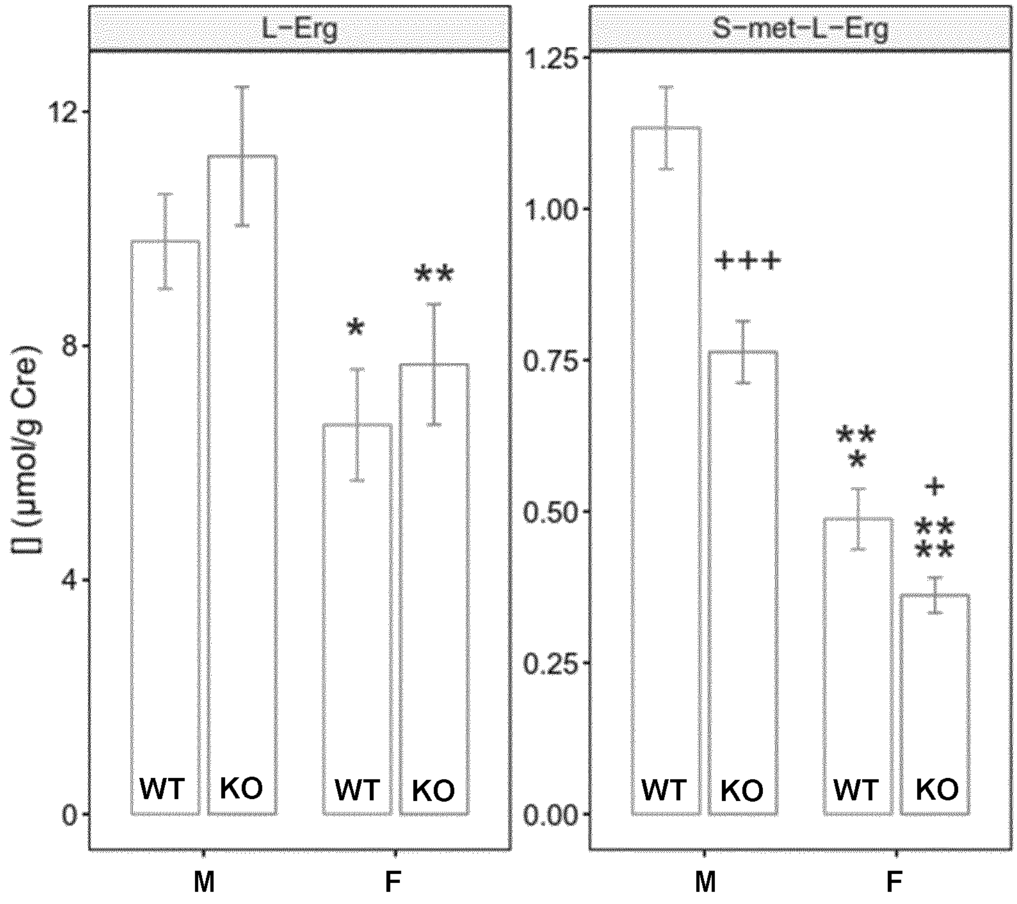
FIG. 3. Sex related differences of L-Erg and S-Met-L-Erg concentration urine in mice. L-Erg and S-Met-L-Erg concentration in urine in 6-month-old wt and Slc7a9$^{-/-}$ (KO) mice. The bars indicate the mean±SEM. Mann-Whitney probability test value is indicated as *, P≤0.05, , P≤0.01, *, P≤0.001, ****, P≤0.0001 vs. male mice, and +, P≤0.05, +++, P≤0.001 vs. wt mice. "M" represents males, and "F" represents females.

In contrast, gender-related significant changes at 6 months of age were detected in the blood, plasma and RBC concentrations of L-Erg in female cystinuric mice. In blood and RBC an almost 2-fold reduction and a 30% reduction in plasma were observed. Similar situation was observed in the urine of female mice, where an almost 2-fold reduction was in the concentration of S-Met-L-Erg and about a 30% in L-Erg (FIG. 3). Furthermore, RBC concentration of L-Erg was 30% lower in female cystinuric mice and the urine concentration of S-Met-L-Erg in female cystinuric mice was significatively 30% lower than female wt mice.

Differences in L-Erq Concentration in Urine Related to Cystine Calculi Presence

Figure 4A:
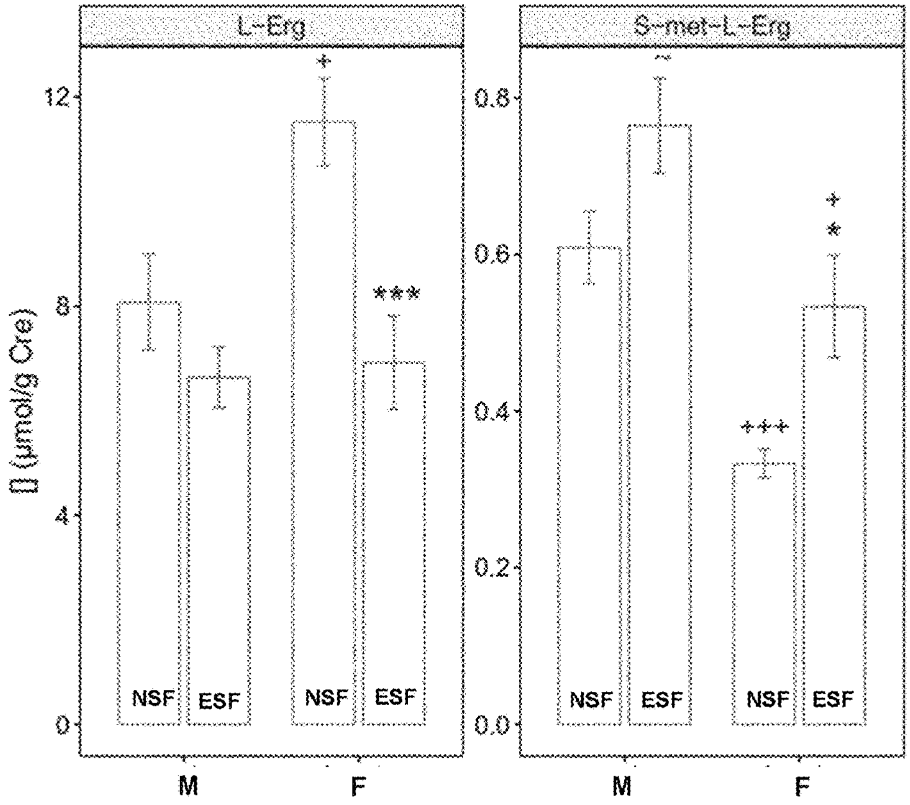
FIG. 4. L-Erg and S-Met-L-Erg urine concentration in stone former and non-former cystinuric mice. L-Erg and S-Met-L-Erg concentration in the urine of 3- (A) and 6-month-old (B) cystinuric mice (Slc7a$^{-/-}$ related to the presence (SF) or absence (NSF) of cystine stones differentiated by sex. The stone-former (SF) mice have been subdivided by the time the stone is detected: ESF, stone detected before 3 months of age and LSF, stone detected after 3 months of age. The bars indicate the mean±SEM. Mann-Whitney probability test value is indicated as ~, P≤0.1, *, P≤0.05, , P≤0.01, *, P≤0.001 vs. non-stone former mice, and +, P≤0.05, ++P≤0.05, +++, P≤0.001 vs. male mice. "M" represents males, and "F" represents females.
Figure 4B:
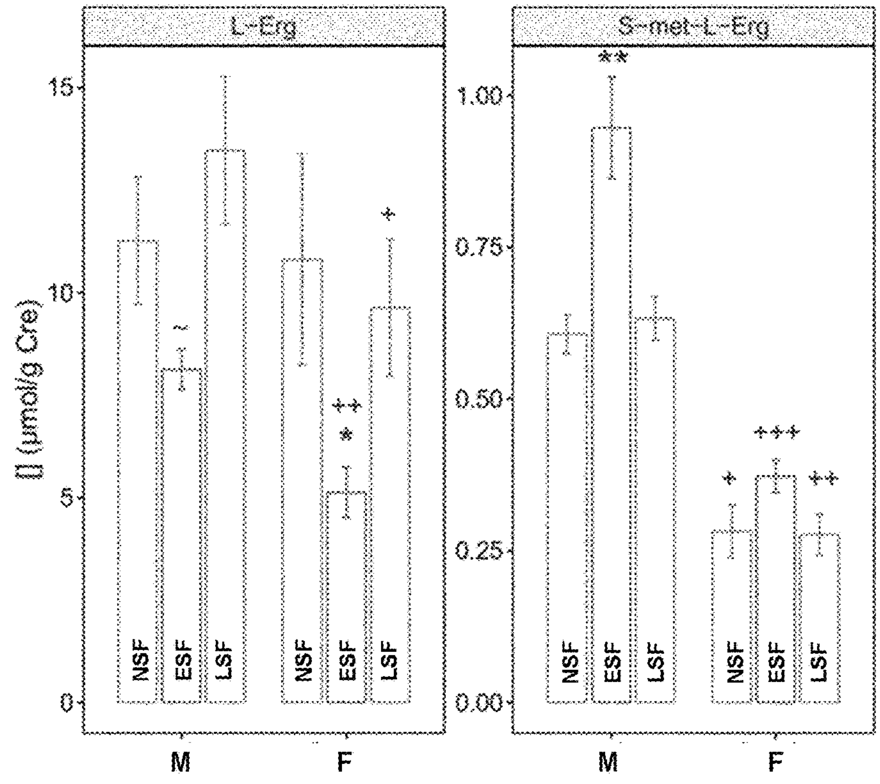

One of the hallmarks of cystinuria is the presence of calculi of cystine stones in cystinuric patients and mice. Therefore, the inventors analyzed the urine concentration of L-Erg and S-Met-L-Erg in stone and non-stone former cystinuric mice at 3- and 6-months of age (FIG. 4). L-Erg urine concentration was significatively lower in early stone former (ESF) female mice (FIG. 4A), meanwhile S-Met-L-Erg was higher in ESF females at 3 months of age (FIG. 4A) and in ESF males at both ages (FIG. 4A-B, P=0.062 for 3 months-old males). Differences between both sexes could also be identified for both L-Erg and S-Met-L-Erg at both ages being the concentration generally lower in females, except for the L-Erg concentration at 3 months of age (FIG. 4A-B). The inventors investigated if the urine concentration of S-Met-L-Erg could be used to differentiate the lithiasic phenotype in mice by the means of a Receiver operator characteristic (ROC) curve, and obtained an area under the curve over 0.65, which indicates that S-met-L-Erg can be used as a lithiasic biomarker.

As S-Met-L-Erg is a subproduct of L-Erg metabolism the inventors investigated then if the ratio between S-Met-L-Erg and L-Erg showed differences related to the lithiasis phenotype. As shown in FIG. 5A, the ratio in stone former (SF) mice is, in general, significatively 2- to 3-fold lower than in non-stone former (NSF) mice. As this result was so clear the inventors investigated if the ratio between urine concentration of S-Met-L-Erg and L-Erg could be used to differentiate the lithiasic phenotype in mice by the means of a Receiver operator characteristic (ROC) curve. As shown in FIG. 5B, the area under the curve over 0.8 suggests the possibility of using this ratio as a lithiasic biomarker in cystinuric mice. The inventors wondered if there were any differences in the performance of the ratio according to age or sex, being in all cases very similar or slightly better.

The inventors also investigated if there was a correlation between the size of the cystine stone (determined as the dry weight) and the ratio and observed a light correlation (r=0.28, p=0.084) between both variables.

As L-Erg has been shown to be transported by OCTN1 (Slc22a4) and that Slc22a4$^{-/-}$ mice lack L-Erg in the kidneys, the inventors crossed the Slc22a4$^{-/-}$ mice with Slc7a9$^{-/-}$ mice to generate the double KO (Slc7a9$^{-/-}$ Slc22a4$^{-/-}$) to observe if there were differences in the proportion of mice that show the lithiasic phenotype.

Like in the Slc7a9$^{-/-}$ mice, the percentage of female lithiasic mice was significantly higher than in males for all Slc22a4 genotypes. The percentage of lithiasic mice was an 8% higher for those mice KO for Slc22a4$^{-/-}$, suggesting that OCTN1 is a genetic modulator of cystine lithiasis in mice. This gene is also present in humans (NCBI Gene ID 6583, or UniProt KB data base ID Q9H015, version 3 of sequence of May 1, 2007), thus is likely that same mechanism applies to this specie. A striking result was that the percentage of lithiasic females was higher than males except for the Slc7a9$^{-/-}$ Slc22a4$^{+/-}$ (Heterozygous for Slc22a4) at 40 weeks of age, age at which the percentage of lithiasic males shows no differences related to Slc22a4 genotype.

To better understand this result, the inventors analyzed the amount of L-Erg and S-Met-L-Erg in the urine of mice lacking OCTN1 (Slc22a4) in the cystinuric background (Slc7a9$^{-/-}$) at 3 months of age. L-Erg was detectable in mice urine to similar levels in Slc7a9$^{-/-}$ and wt mice, but the amount of S-Met-L-Erg was a significative 50% lower in Slc7a9$^{-/-}$ mice (P=0.0022). Knocking out Slc22a4 in the Slc7a9$^{-/-}$ background produced a significative reduction of L-Erg (P=0.0382 for Slc22a4$^{+/-}$ and P=0.0138 for Slc22a4$^{-/-}$) and S-Met-L-Erg concentration in urine, being the concentration of S-Met-L-Erg bellow the quantification limits of the method used.

As expected, Slc22a4$^{-/-}$ mice showed lower concentration of L-Erg than Slc22a4$^{+/-}$ mice. This data suggests that another transporter might be involved in the absorption of L-Erg from the diet but that OCTN1 is needed for L-Erg transport into the cells as no metabolite product (S-Met-L-Erg) could be detected in urine.

Example 2: Treatment of Cystine Lithiasis in a Cystinuria Mouse Model

Methods

Mice care was as indicated in Example 1.

L-Erq Treatments

Three different treatments were applied to mice: 1-month, 3-month to lithiasic mice (subchronic) and 6-month (chronic exposure). In all cases L-Erg was administered in the drinking water.

For the 1-month treatment, L-Erg was provided to eight 3-month old male and female mice at 15 or 60 mg/L for 4 weeks in standard cages with free access to water and food to 8 mice (4 males and 4 females).

For the evaluation of L-Erg effect on lithiasic mice, 15 mice (8 males and 7 females) were treated with 60 mg/L L-Erg on the drinking water and 13 mice (4 male and 9 females were left untreated as control. Mice were 10.9-26-9 weeks-old at the beginning of the treatment period with a mean age of 15.3±1.4 and 16.9±1.01 weeks of age for control and L-Erg treated, respectively. During the 3-month treatment water intake and mice weight was monitored weekly.

For the chronic exposure (6-month treatment), 4-6 mice per cage were treated since weaning for 6 months. To control L-Erg dose, water intake and mice weight were monitored and L-Erg concentration in drinking water was adjusted to get 16 mg/kg·day dose every 3 days for the first month and weekly afterwards. All mice were caged in metabolic cages individually the last week of the treatment to collect urine where water intake and mice weight were monitored daily.

Cystine Calculi Detection by X-Ray In Vivo Imaging

Isoflurane anesthetized mice were subjected to X-ray imaging for lithiasis detection and follow-up with an IVIS Lumina XR Series III (Caliper Lifescience-Vertex Techniques) following manufacturer's imaging parameters at the age indicated in the corresponding figure legends with a calibration curve of cystine stone of known weights. Stone quantification was done using Living Image Software, provided with the instrument, by manually delimiting stone area and the estimated weight was interpolated from the calibration curve.

For the growth rate analysis, a linear regression model was used when more than 2 data points where available. The slope of the regression line in the model was used as the growth rate.

Sample Collection

During the last week of any treatment period, mice were individually housed in metabolic cages for 4 days with the first day as an adaptation period. Mice weight, water and food intake, and excreted urine were monitored daily. 24 h urine samples were collected and kept at −80° C. until further analysis with 50 μL thymol 10% in isopropanol as preservative. pH was determined with a pHmeter (cat. no. 5209, Crison), and the redox potential with an ORP electrode (cat.no. 5265, Crison) at room temperature on a micropH 2000 (Crison).

On the last day, mice were anesthetized with isfluorane and blood removed through intracardiac puncture and kidneys were harvested, weighted and stored at −80° C. until further use. Cystine stones, if present, were removed, dried, weighted and stored at RT.

Analysis of Compound Concentrations in Urine

Creatinine concentrations in thawed urine samples were determined with Creatinine Assay Kit (Sigma) as indicated by manufacturer after filtering through 10 kDa MWCO spin filters (Amicon Ultra 0.5 mL, Millipore).

L-Erg and S-Met-L-Erg analysis in urine were determined as in Example 1. For the determination of transulfuration pathway metabolites concentration, frozen kidneys were grinded using a pre-cooled mortar and pestle on dry ice. Then, 100 mg of powdered kidney were homogenized in 400 μL PBS supplemented with 10 mM NEM. To induce protein precipitation, PCA at 4% was added and samples were centrifuged at 4° C. for 15 min at 10,000 rpm in a microfuge. Supernatants were transferred to a new tube and stored at −80° C. until further analysis. Intracellular content of transulfuration pathway metabolites was determined by U PLC-MS/MS (Escobar J, et al. Development of a reliable method based on ultra-performance liquid chromatography coupled to tandem mass spectrometry to measure thiol-associated oxidative stress in whole blood samples. *J. Pharm. Biomed. Anal.* 2016; 123: 104-112). Protein pellets were resuspended in 400 μL 1M NaOH and the supernatant used to determine total protein concentration by BCA Protein Assay Kit (ThermoScientific).

L-Erg-Cys In Vitro Binding Assay

The reactivity of L-Erg with itself and with Cys was assayed in vitro at two conditions pH=7.2 in 0.2M $Na_2HPO_4$ and pH=11 in boric acid buffer (ref. 33650-1L, Fluka) at RT for 17 h. The presence of L-Erg-L-Erg and L-Erg-Cys dimers, and cystine was determined by LC/MS-MS.

Statistical Analysis

Non-parametric analysis (Wilcoxon-Mann-Whitney test) were used to assess significance using Rstudio. Statistical significance is considered positive if $p<0.05$.

Results

Figure 6A:
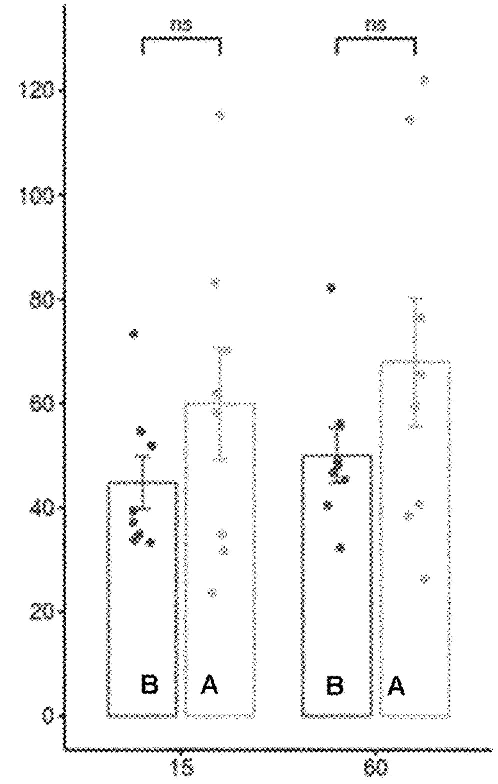
FIGS. 6A-6E. (related with Example 2). Metabolism variations due to L-Erg treatment. Water intake normalized by the mice surface (FIG. 6A), pH (FIG. 6B) and redox potential (FIG. 6C) before (Initial, left bars, "B") and after (Final, right bars, "A") the treatment with different concentrations of L-Erg supplemented in the drinking water. Each dot represents a mouse. Wilcoxon test results. pH and redox potentials could not be determined in all treated mice due to urine volumes bellow the lower limit of the pH and redox electrodes. Urine L-Erg concentration in semi-log scale for visualization purposes (FIG. 6D) and S-Met-L-Erg (FIG. 6E) concentrations before (FIG. 6B) (Initial, left bars) and after (FIG. 6A) (Final, right bars) the treatment with different concentrations of L-Erg supplemented in the drinking water. Each dot represents a mouse and the bars show the mean±SEM. In all panels, ns, non-significant; *p<0.05 with a Wilcoxon signed-rank test. Initial values before treatment correspond to left-side bars in each figure (FIG. 6A-E) and/or for each L-Erg tested dose. Final values after treatment correspond to right-side bars in each figure (FIG. 6A-E) and/or for each L-Erg tested dose. The x-axis represents L-Erg (mg/L), and the y-axis represents Water Intake/Weight$^{2/3}$ ratio (ml/kg$^{2/3}$) (FIG. 6A); pH (FIG. 6B); ORP (mV) (FIG. 6C); [L-Ergothioneine in urine (μM) (FIG. 6D); and [S-Methyl-L-30 ergothioneine] in urine (μM) (FIG. 6E).
Figure 6B:
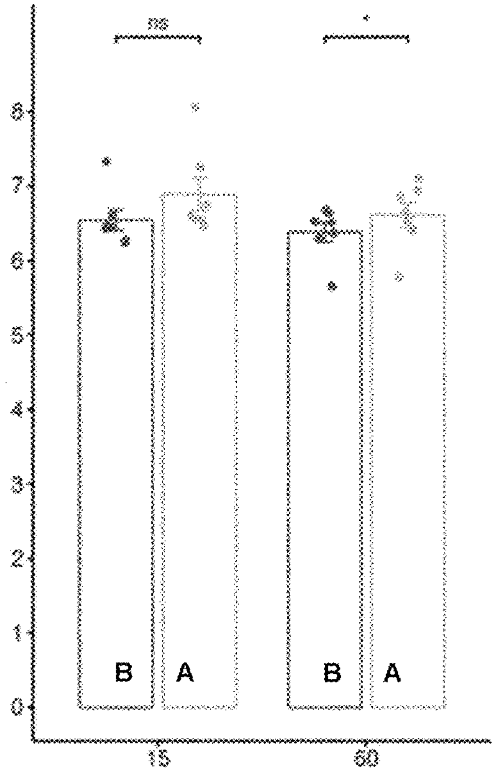
Figure 6C:
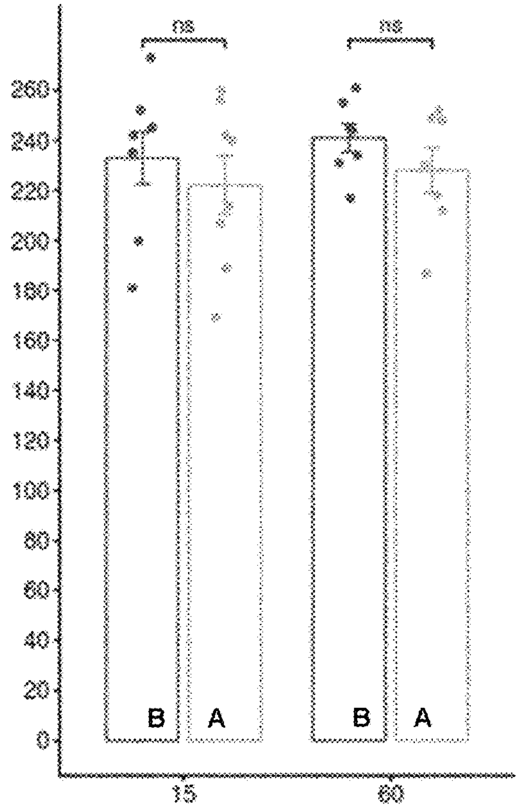
Figure 6D:
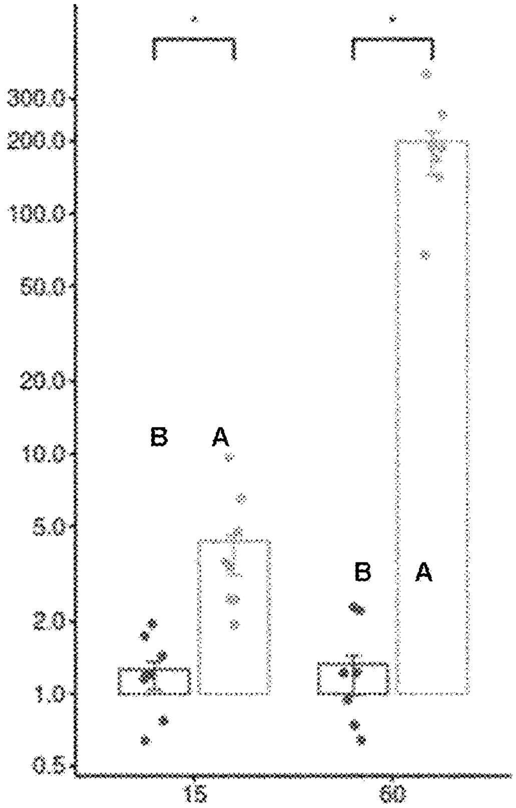
Figure 6E:
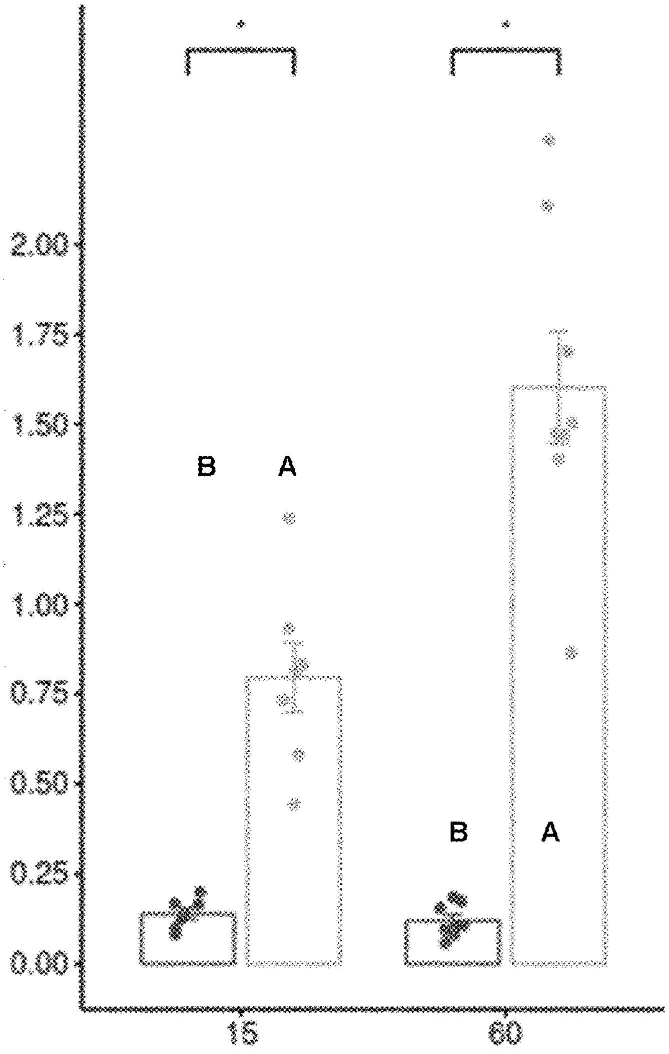

First, there were determined the best working dose for treating the mice by investigating the effects of 1-month L-Erg treatment at two different concentrations in the drinking water, 15 and 60 mg/L, on water intake, and urine pH and ORP and L-Erg concentration. Following observations were done:

i) a statistically non-significant increase ($p=0.11$ and $p=0.08$, respectively) at the end of the treatment at any tested L-Erg concentrations in water intake normalized by surface (FIG. 6A), especially in females (gender data not shown); ii) a statistically significant increase in pH (FIG. 6B) at 60 mg/L and a statistically non-significant increase in pH at 15 mg/L ($p=0.052$), especially in males (data not shown); iii) a statistically non-significant decrease in urine redox status or potential (ORP) (FIG. 6C); and, iv) a statistically significant increase in L-Erg and S-Met-L-Erg concentrations in urine (FIGS. 6D and 6E, respectively). Interestingly, differences in the urine concentration of L-Erg and S-Met-L-Erg were found between both tested conditions. At 15 mg/L, L-Erg and S-Met-L-Erg concentrations increased 3-fold (3.4±0.4) and 6-fold (5.9±0.6), respectively. At 60 mg/L, the increase was 175-fold (174.6±38.4) and 15-fold (14.7±1.9) for L-Erg and S-Met-L-Erg, respectively. These differences suggest that at 60 mg/L, the endogenous pools and metabolism of L-Erg might be close to saturation. To maximize the amount of L-Erg available in urine, the concentration of 60 mg/L of L-Erg in the drinking water was taken for further assays which corresponded to a mean±SEM calculated dose of 13.6±1.6 mg/kg·day (data not shown).

L-Erg Treatment does not Alter Cystine Stone Growth (3 Months)

Figure 7:
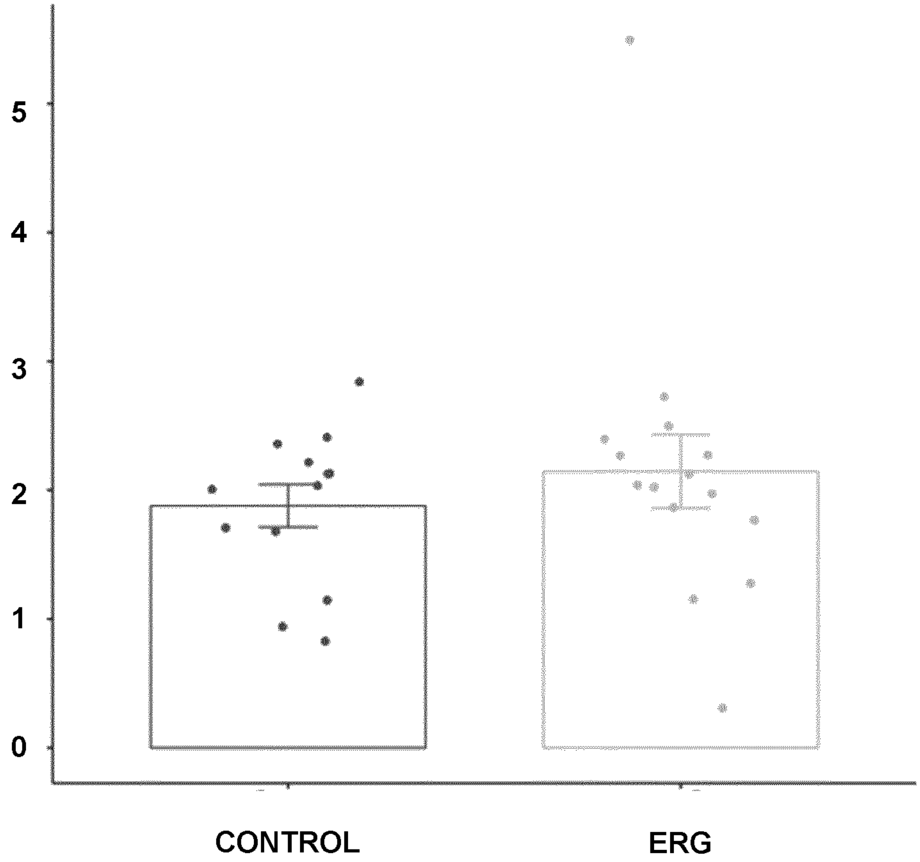
FIG. 7. (related with Example 2). Stone growth rate on lithiasic mice treated with L-Erg. Male and female mice were treated (ERG) or left untreated (C) with 60 mg/L L-Erg in the drinking water for 3-months. The y-axis represents the stone growth rate (mg/day). The bars represent the mean±SEM of the stone growth rate determined monthly by X-ray imaging of 13-15 mice. Each dot represents the cystine stone growth rate determined for each mouse.

It was first checked the effect of L-Erg treatment (60 mg/L on drinking water) on cystine stone progression in lithiasic mice by monitoring monthly the cystine stone growth by X-rays during 3 months in both treated and untreated mice. No effect ($p=0.61$) of the treatment on the cystine stone growth at the tested conditions (FIG. 7) was observed. As cystinuric mice can have multiple or single stones, it was also analyzed if there were effects on each type. No statistically significant effect was observed either for single or multiple stones ($p=0.78$ and $p=0.41$, respectively; (data not shown). To see the effect of the treatment on different metabolic parameters, it was also analyzed the effects on urine pH and redox status and surface corrected water intake and observed no differences on L-Erg treated animals before and after treatment (data not shown). Estimated mean±SEM L-Erg dose during the experiment was (17.24±0.69 mg/kg·day).

L-Erg Treatment Prevents or Delays Cystine Stone Onset (Erg Treatment 6 Months)

Figure 8A:
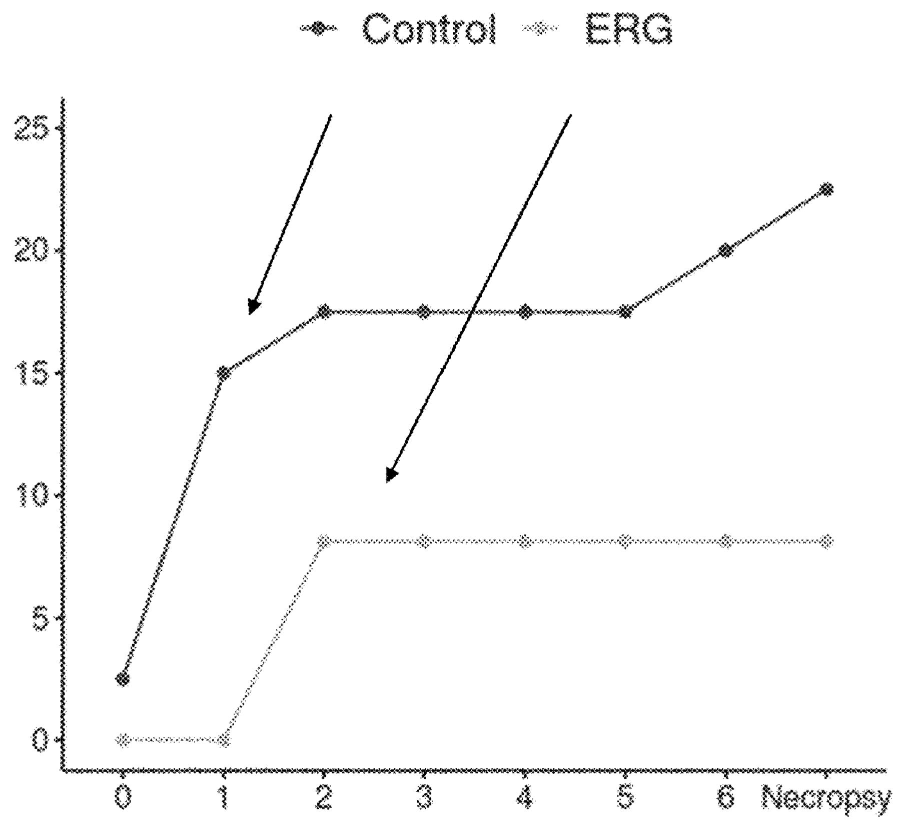
FIGS. 8A-8D, (related with Example 2). Effect of a chronic (6-month) L-Erg treatment on cystine lithiasis onset and metabolic parameters.
Figure 8B:
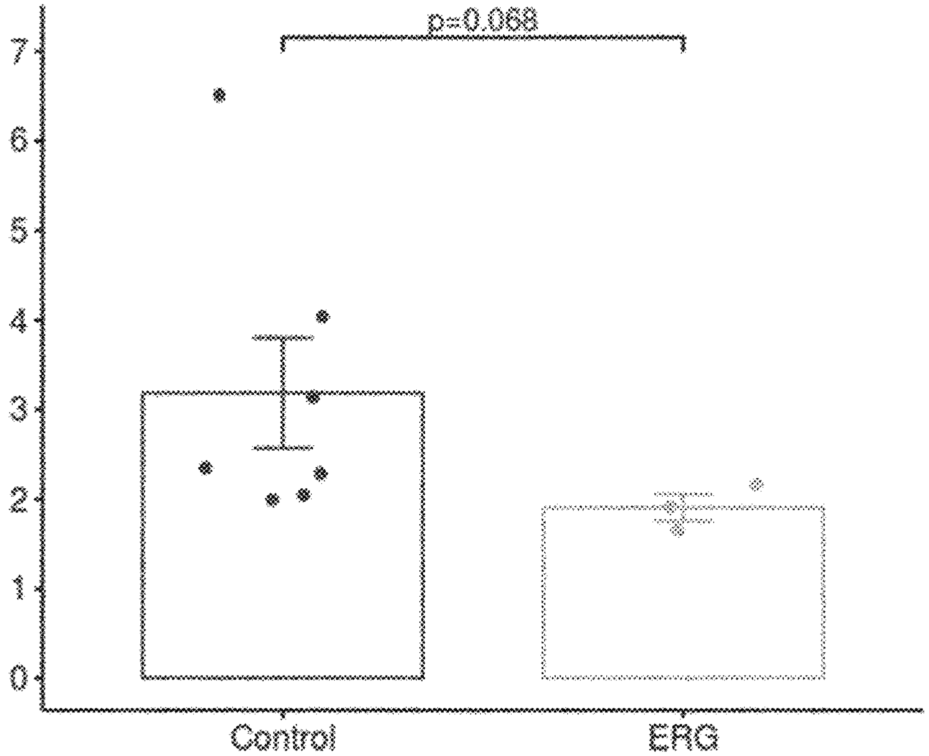

Then it was tested if L-Erg had any effect on cystine stone formation by treating cystinuric mice since weaning for 6 months. Considering the previous experiments on adult mice, target dose of 16 mg/kg·day was set. To achieve it on growing mice, mice growth and water intake were monitored during the whole experiment and adjusted L-Erg concentration in drinking water considering the water intake corrected by body surface based on Tordoff et al results (see Tordoff M G, Bachmanov A A, Reed D R. Forty mouse strain survey of water and sodium intake. *Physiol. Behav.* 2007; 91: 620-31). The estimated mean±SD dose over the 6-month period was 16.25±6.29 (data not shown). To analyze the effect on lithiasis onset, treated and untreated mice were followed by X-ray imaging every month during the 6-month treating period. It was observed a 50% reduction in the number of lithiasic mice, a delayed lithiasis onset (FIG. 8A) independently of the mice sex (data not shown) and an almost statistically significant reduction in the stone growth in the L-Erg treated group (FIG. 8B).

Figure 8C:
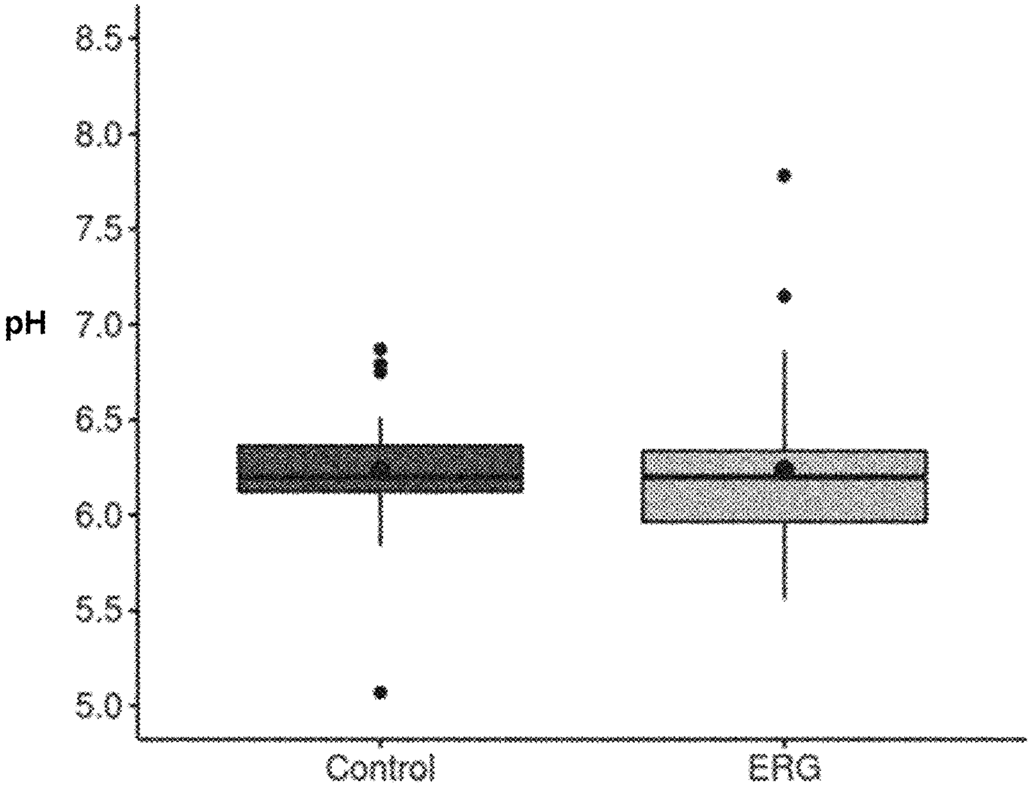
Figure 8D:
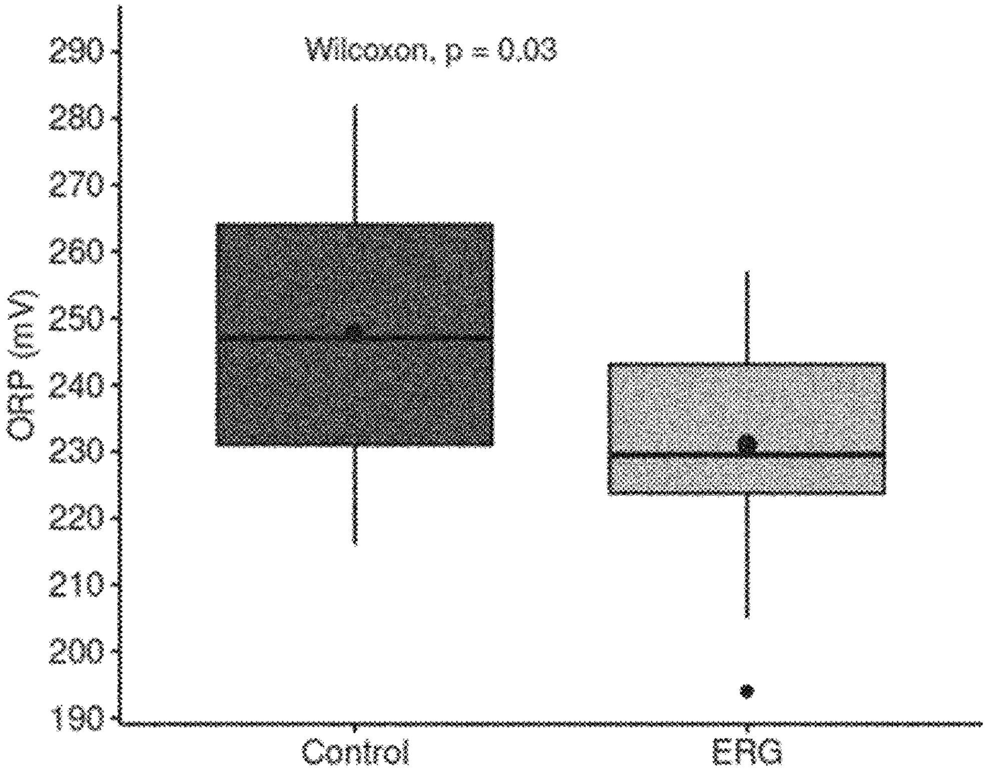
Figure 9A:
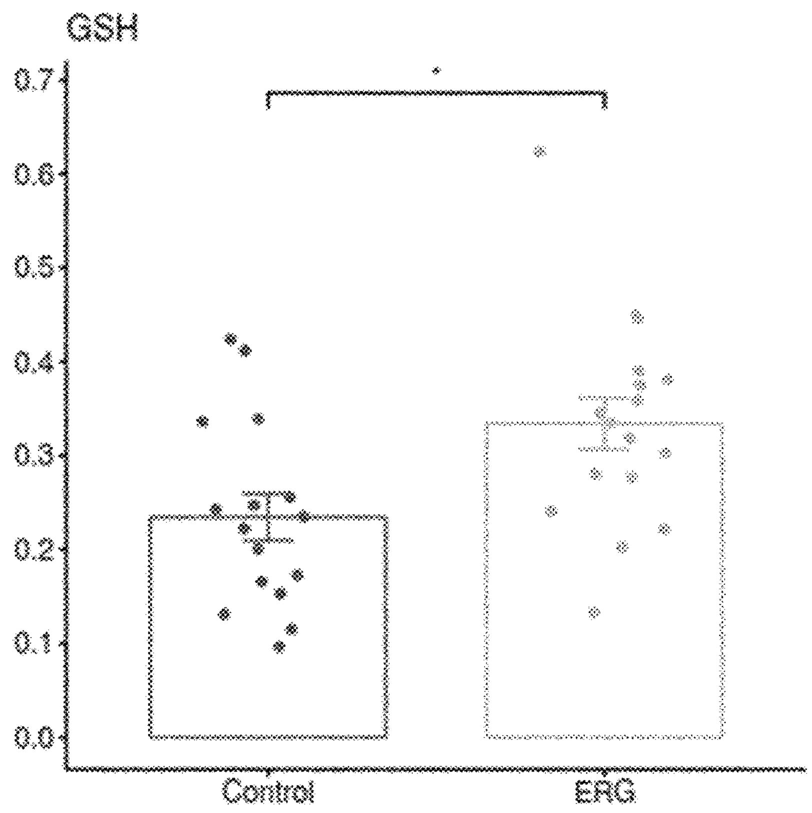
FIGS. 9A-9I (related with Example 2). L-Erg increases the intracellular renal concentration of components of the transulfuration pathway. This figure shows intracellular content of those metabolites of the transulfuration pathway in the kidneys of chronically treated and untreated mice. The y-axis represents nmol/mg protein. Glutathione (GSH) in (FIG. 9A); oxidized glutathione (GssG) in (FIG. 9B); ratio GSH/GssG in (FIG. 9C); Cysteine (Cys) in (FIG. 9D); cystine (CssC) in (FIG. 9E); ratio Cys/CssC in (FIG. 9F); S-adenosylhomocysteine (SAM) in (FIG. 9G); S-adenosylmethionine (SAM) in (H); ratio SAM/SAH in (FIG. 9I); Methionine (Met) in (FIG. 9J); gamma-Glutamylcysteine (gammaGluCys) in (FIG. 9K); and Cystathionine in (FIG. 9L). Each dot represents a mouse and the bars show the mean±SEM. In all panels; *p<0.05, , P:::; 0.01, *, P:::; 0.001, ****, P:::; 0.0001 with a Wilcoxon signed-rank test.
Figure 9B:
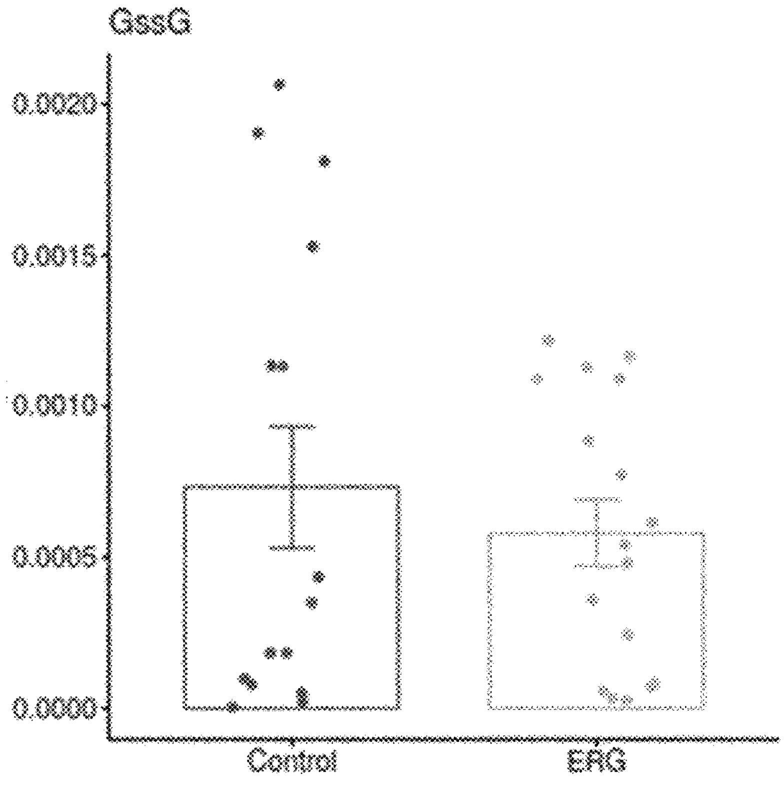
Figure 9C:
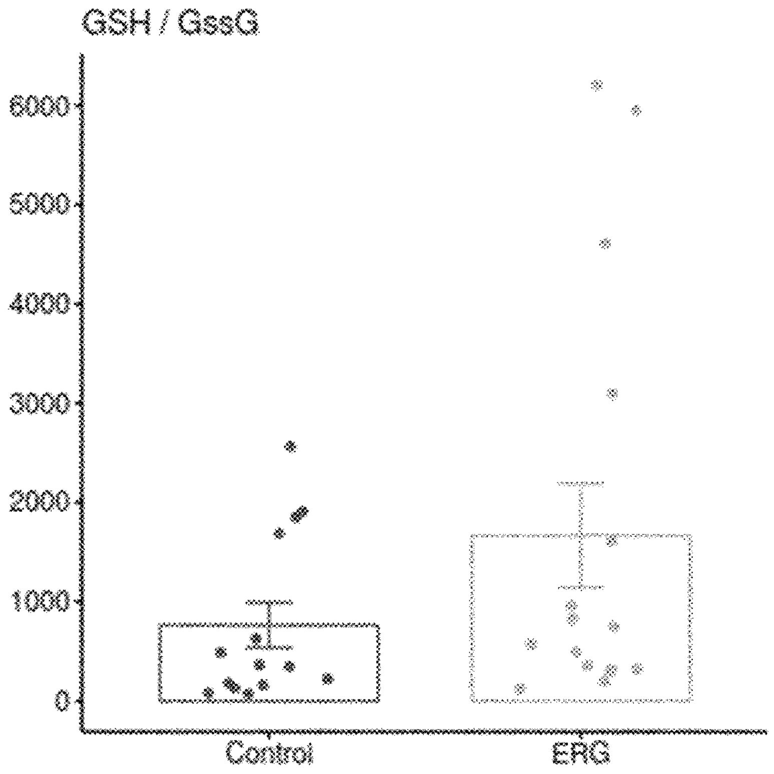
Figure 9D:
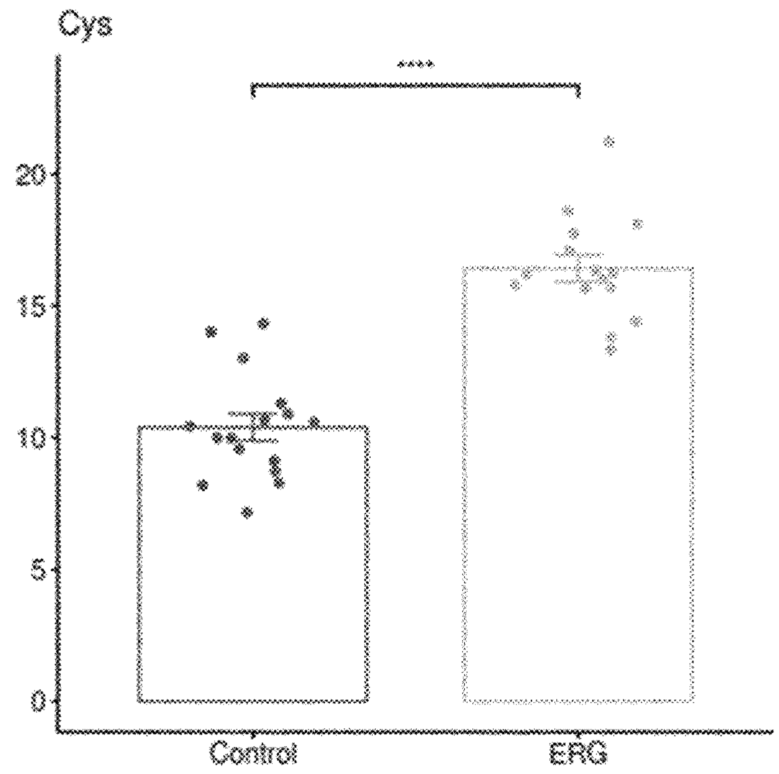
Figure 9E:
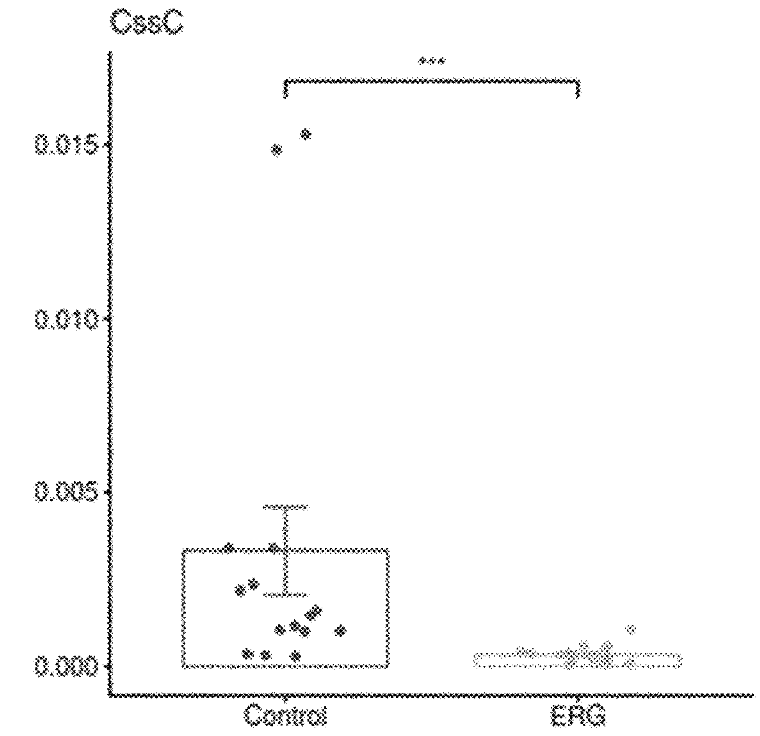
Figure 9F:
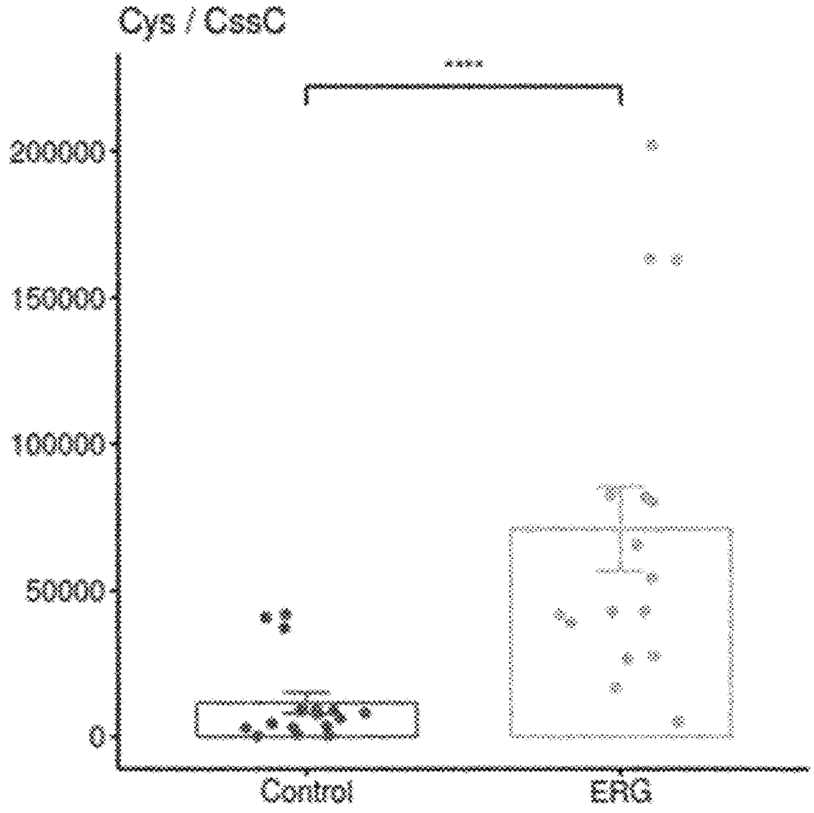
Figure 9G:
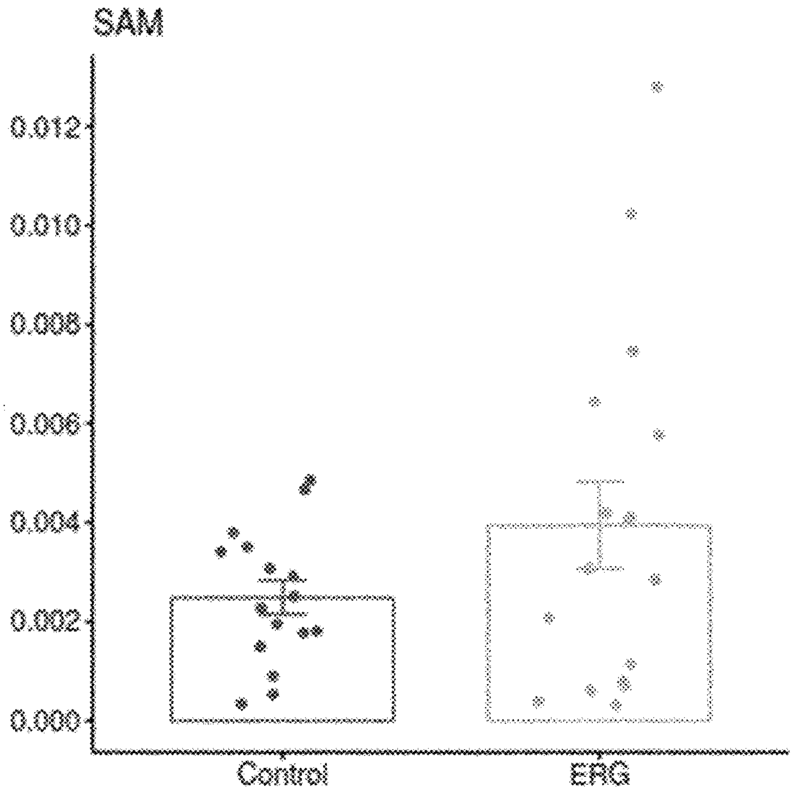
Figure 9H:
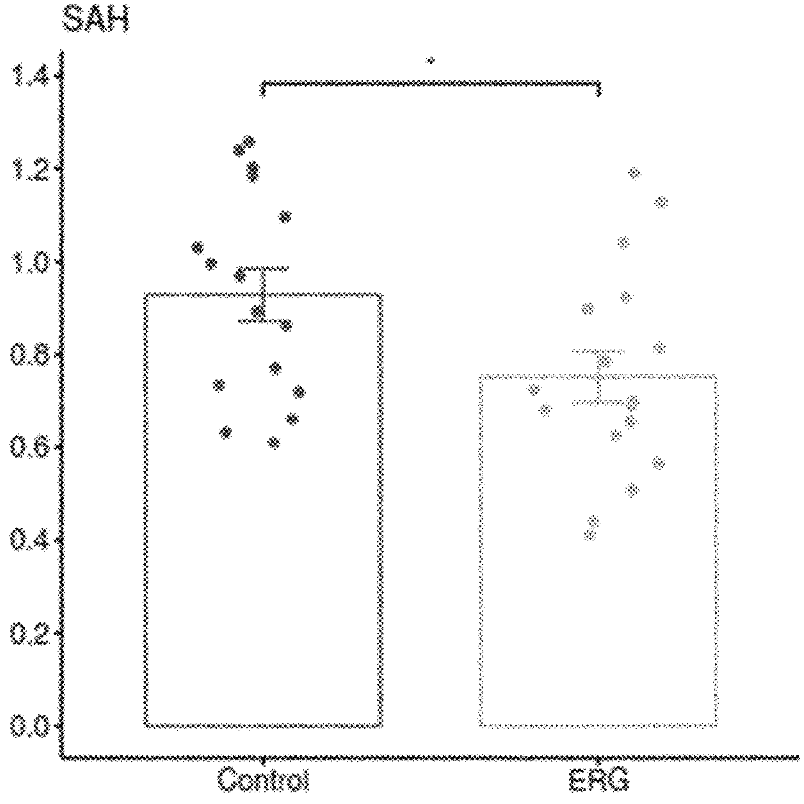
Figure 9I:
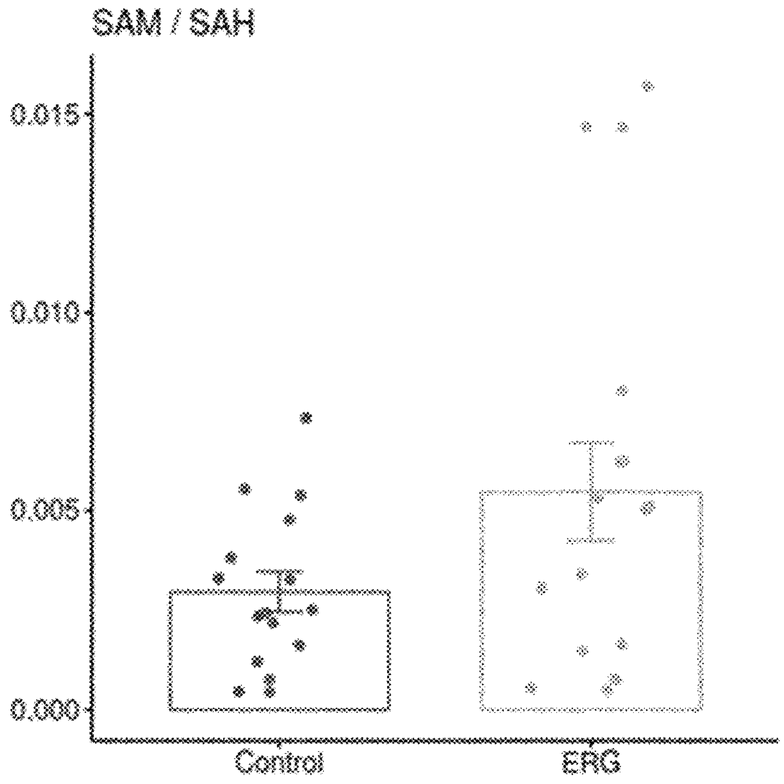
Figure 9J:
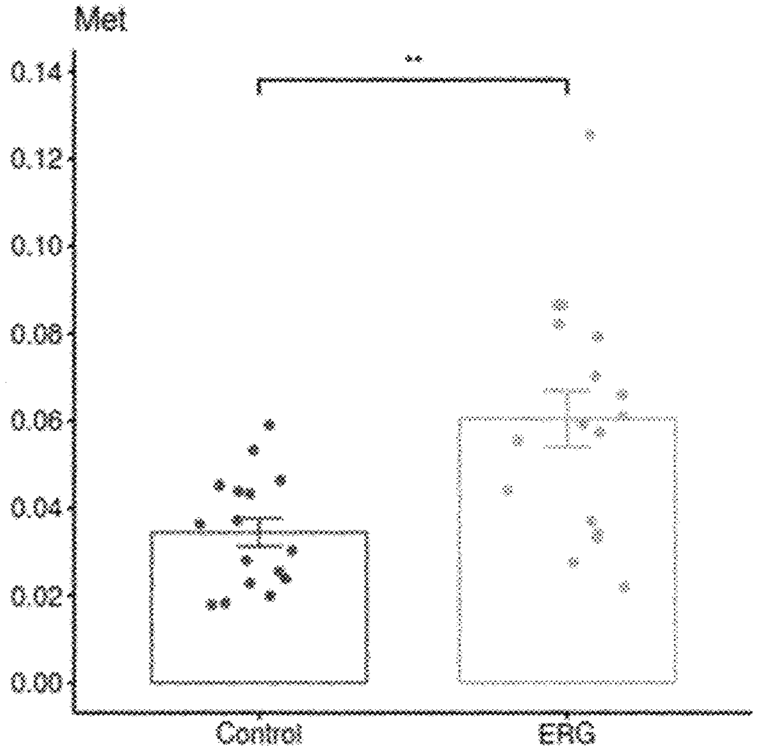
Figure 9K:
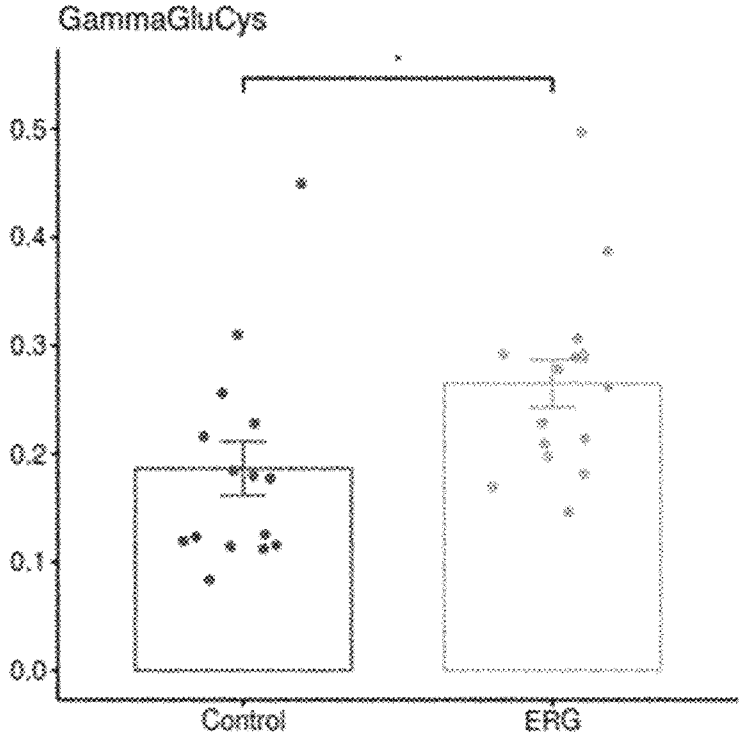
Figure 9L:
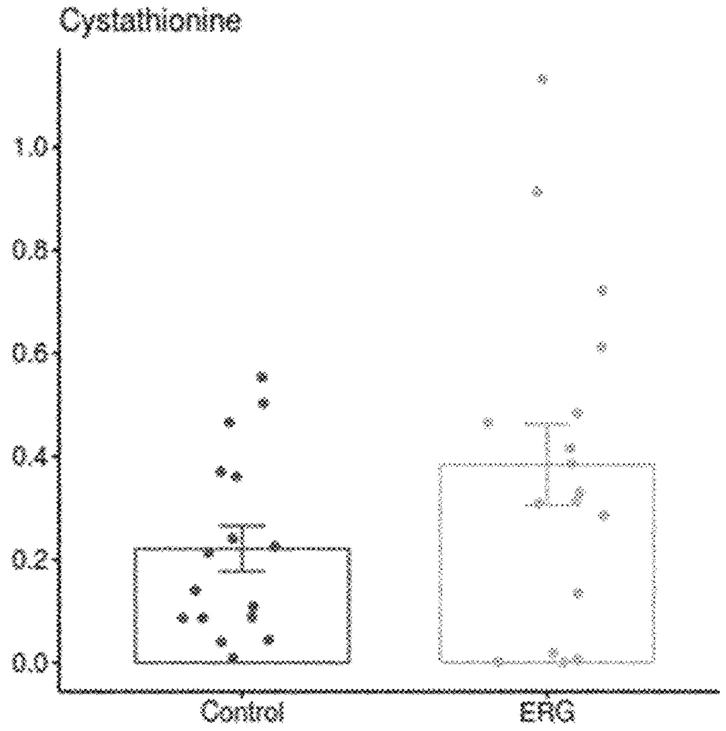

To analyze the effect of the long treatment, urine pH and redox potential were determined observing no differences in urine pH (FIG. 8C) and a statistically significant more reduced urine in L-Erg treated mice (FIG. 8D). This chronic treatment showed no effects on either the water intake or mouse weight (data not shown).

L-Erg Increases the Intracellular Renal Concentration of Components of the Transulfuration Pathway The antioxidant capabilities of L-Erg might explain the reduction of the urine redox potential, but, by itself, do not explain the diminished lithiasis and the differences observed on the stone growth rate between the two different treatments performed. To get some insight on the mode of action of L-Erg on cystine lithiasis the formation of dimers L-Erg-Cys in vitro at two conditions pH=7.2 and pH=11 by LC/MS-MS was first analyzed (data not shown). Neither L-Erg-Cys, nor L-Erg-L-Erg dimers were detected which suggests that L-Erg mode of action does not imply the reduction of L-Cys concentration by quenching part of it.

The lower ratio between urine concentrations of S-Met-L-Erg (the L-Erg metabolite) and L-Erg clearly in lithiasic compared to non-lithiasic mice (see data in Example 1) points to the involvement of intracellular mechanisms in cystine lithiasis. In this sense, L-Erg has been reported to activate glutathione (GSH) synthesis by upregulating Nrf2 (Kerley R N, et al. The potential therapeutic effects of ergothioneine in pre-eclampsia. *Free Radic. Biol. Med.* 2018; 117: 145-157) and, in a proteomic approach to identify differential protein expression between cystinuric and wt mice, it has been shown that some enzymes involved in GSH synthesis like Anpep (Anpep), Gpx1 (Gpx1) and Gstt1 (Gstt1) and cystine metabolism like Cdo1 (Cdo1) were downregulated in the cystinuric mice renal brush borders. Based on this, the intracellular content of those metabolites of the transulfuration pathway in the kidneys of chronically treated and untreated mice were analyzed. Data are depicted in FIG. 9 (A to L), GSH (1.4×), Cys (1.6×), gamma-Glutamylcysteine (1.7×) and Met (1.7×) intracellular concentrations were significantly increased about 1.5 times and those of cystine (11.1×) and S-adenosylhomocysteine (SAH), (1.2×) significantly decreased in L-Erg treated mice. Interestingly, the GSH/GSSG, the Cys/CssC, and the SAM/SAH ratios were increased in L-Erg treated mice (2.1, 6.1 and 1.8 times, respectively). GSSG is oxidised glutathione; CssC is cystine; SAM; is S-adenosylmethionine.

Discussion

The chosen drug delivery system could be considered as less appropriate for controlling the dose. It is true that it is prompt for more variability, but as L-Erg blood and plasma concentrations remain significatively higher for 6 weeks, and the urine concentration forl week after the administration end of an equivalent of 5 mg/kg·day, it is difficult to argue that a drop in the dose of L-Erg taken by mice could be responsible of the observed lithiasis in treated animals.

Preliminary results in the Slc7a9$^{-/-}$ mice have shown significant different concentrations of the metabolites of the transulfuration pathway in kidney. Among those with decreased concentration were: GSH (4.5×), GssG (17.9×), SAM (2.4×), Met (23.8×) and cystathionine (10.3×). Among those with increased concentrations were Cys (6.7×), cystine (CssC, 3.8×), SAH (9×) and gamma-glutamylcysteine (2.1×). Both GSH/GssG and Cys/CssC ratios were increased in cystinuric male mice about 6 times, meanwhile the SAM/SAH ratio was 21 times decreased. This data suggests the existence in cystinuric a reduced methylation capability of the kidney in cystinuria and a reduced activity within the transulfuration pathway. The unexpected elevated Cys content in kidney could suggest a mechanism to compensate the reduced GSH content in an effort to overcome the limitations in controlling any oxidative damage as suggested by Banjac et al., "The cystine/cysteine cycle: a redox cycle regulating susceptibility versus resistance to cell death"; 2008; Oncogene; vol. 27(11); pp. 1618-28. Chronic treatment of L-Erg has been shown to increase the expression of glutathione reductase, catalase and superoxide dismutase in vascular endothelial human cells and induce Nrf2/ARE-mediated antioxidant genes in UVA irradiated human keratinocytes. In this content a general induction of the transulfuration pathway in L-Erg treated mice except for GssG, CssC and SAH was observed. In which extend this increase in reducing capability in kidney is related to the lower redox potential in urine is still unknown and subject for further experiments.

Unexpectedly, differences in the effect of L-Erg treatment in the cystine stone progression between both tested treatments have been observed: after stone onset or preventive (before stone onset). As the cystine stone growth rates in the control mice are different between both experiments (about 2 mg/day and about 3 mg/day, respectively) any statistical artifact cannot be completely ruled out, since the amount of cystine stones that could be followed during the preventive experiment was low or differences due to intersibling variability could have a particular weight.

Example 3. Urine Redox Status or Potential (ORP) as Marker of Prognosis in Cystinuric Animals Inventors realized that ORP in urine of cystinuric mice not forming cystine stones was lower than urine ORP in mice forming stones. Thus, this parameter (measured as indicated in Example 2) is also proposed for the in vitro differential prognosis in cystinuric animals, including humans.

Methods

Mice care was as in Example 1

Sample Collection

Mice were individually housed in metabolic cages for 4 days with the first day as an adaptation period. Mice weight, water and food intake, and excreted urine were monitored daily. 24 h urine samples were collected and kept at −80° C. until further analysis with 10 mM sodium azide as preservative. The redox potential was determined in fresh urine with an ORP electrode (Crison) at room temperature on a micropH 2000 (Crison).

Results

ORP is Higher in Stone-Forming Mice

Figure 10:
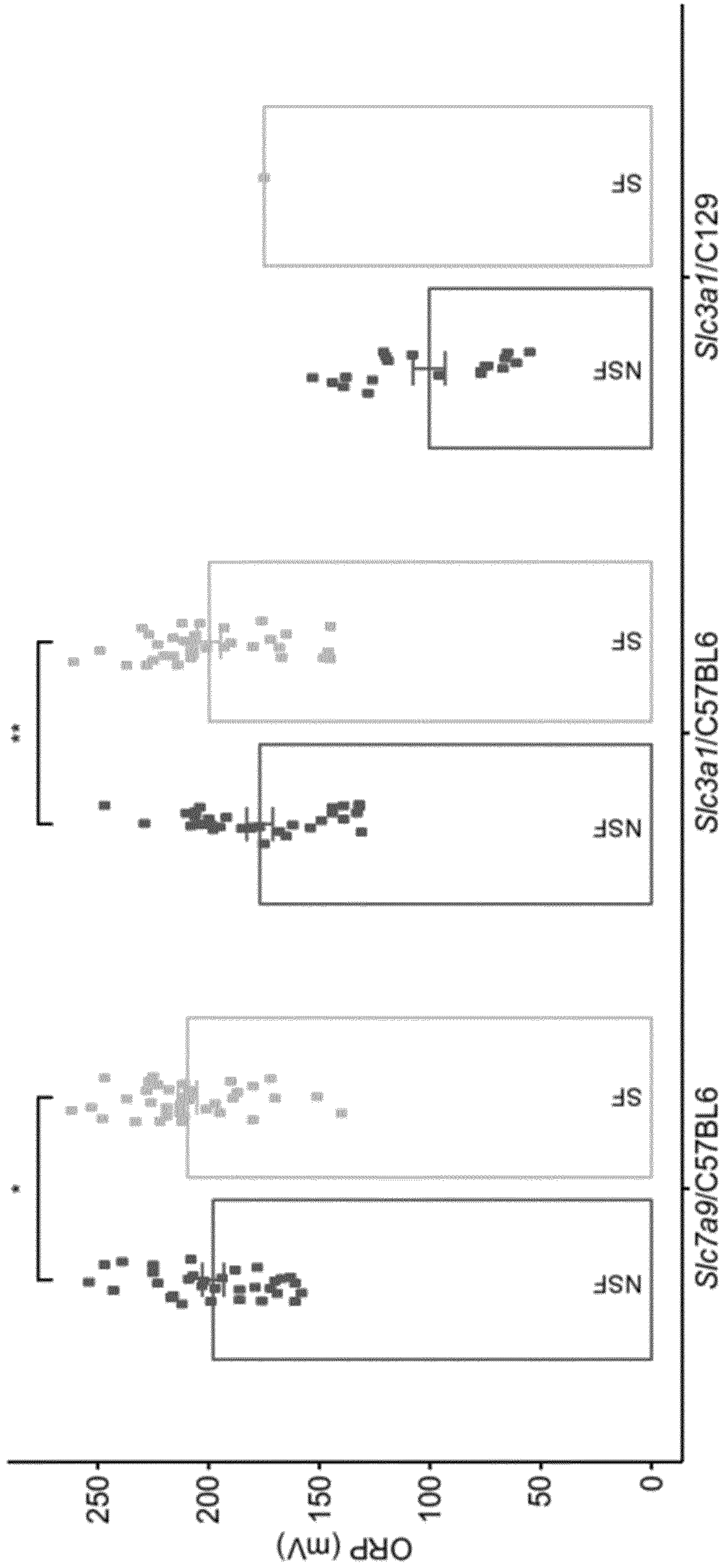
FIG. 10 (related with Example 3). Urine ORP(mV) in cystinuric mice from two different mice models (Slc7a9$^{-/-}$ or Slc3a1$^{D140G}$) for cystinuria in a C57BL6/J genetic background. Preliminary data from the type-I cystinuria mice model 12952/SvPasCrl (Slc3a1$^{E383K}$). *p<0.05, **, P≤0.01 with a Wilcoxon signed-rank test.

Urine ORP was significatively higher in cystinuric mice from two different mice models (Slc7a9$^{-/-}$ (Feliubadaló et al., supra) or Slc3a1$^{D140G}$) for cystinuria in a C57BL6/J genetic background. Slc3a1$^{D140G}$ model is disclosed by Peter et al., "A mouse model for cystinuria type I", Hum Mol Genet. —2003 vol. 1; 12(17), pp.: 2109-20. Preliminary data from the type-I cystinuria mice model 12952/SvPasCrl (Slc3a1$^{E383K}$) showed similar results considering the very limited amount of sporadic cystine stones produced by the model when assayed. All these data are depicted in FIG. 10, and clearly indicate that urine ORP could be useful for the diagnosis or prognosis of cystine lithiasis. When considering both genders, although the tendency is kept for all groups, only the males from the Slc7a9$^{-/-}$ and the females from Slc3a$^{D140G}$ in C57BL6/J showed significant decreases in urine ORP (gender data not shown).

Interestingly, the urine ORP in the non-stone former group of the 12952/SvPasCrl mice model is significantly lower ($p=1.9e^{-09}$) than that of the Slc3a1$^{D140G}$ mice model, although the same gene is affected in both models, suggesting the existence of genetic factors involved in urine ORP.

CITATION LIST

Halperin E C et al., "The use of D-penicillamine in cystinuria: efficacy and untoward reactions", Yale J Biol Med., 1981, vol. 54(6), pp. 439-46.

Burtis C. A. et al., 2008, Chapter 14, section "Statistical Treatment of Reference Values".

Kato Y. et al., "Gene knockout and metabolome analysis of carnitine/organic cation transporter OCTN1", *Pharm. Res.,* 2010; vol 27, pp. 832-40.

Sotgia S. et al. "Plasma L-ergothioneine measurement by high-performance liquid chromatography and capillary electrophoresis after a pre-column derivatization with 5-iodoacetamidofluorescein (5-IAF) and fluorescence detection". Antopolsky M, ed. *PLoS One* 2013; vol. 8: e70374

Zinellu A. et al., "Assay for the simultaneous determination of guanidinoacetic acid, creatinine and creatine in plasma and urine by capillary electrophoresis UV-detection", *J. Sep. Sci.,* 2006

Escobar J, et al. "Development of a reliable method based on ultra-performance liquid chromatography coupled to tandem mass spectrometry to measure thiol-associated oxidative stress in whole blood samples$. *J. Pharm. Biomed. Anal.* 2016; 123: 104-112 Tordoff M G, Bachmanov A A, Reed D R. Forty mouse strain survey of water and sodium intake. *Physiol. Behav.* 2007; 91: 620-31

Kerley R N, et al. The potential therapeutic effects of ergothioneine in pre-eclampsia. *Free Radic. Biol. Med.* 2018; 117: 145-157

Feliubadaló et al "Slc7a9-deficient mice develop cystinuria non-I and cystine urolithiasis" Hum Mol Genet 2003; vol 12; pp. 2097-2108

Peter et al., "A mouse model for cystinuria type I", Hum Mol Genet. —2003 vol. 1; 12(17), pp.: 2109-20.

Banjac et al., "The cystine/cysteine cycle: a redox cycle regulating susceptibility versus resistance to cell death"; 2008; Oncogene; vol. 27(11); pp. 1618-28.

The invention claimed is:

1. A method of treating a renal lithiasis or cystinuria and/or delaying stone formation and/or delaying stone growth in a subject having cystinuria, comprising administering to the subject a therapeutically effective amount of Ergothioneine.

2. The method of claim 1, wherein the Ergothioneine is administered with a compound selected from the group consisting of an additional cystine-solubilizing agent, L-cystine dimethyl ester, L-cystine methyl ester, L-cystine diamide, lipoic acid, and a combination thereof.

3. The method of claim 1, wherein the renal lithiasis is cystine lithiasis.

4. The method of claim 1, wherein the Ergothioneine is administered in the form of a pharmaceutical composition comprising one or more pharmaceutically acceptable excipients and/or carriers.

5. The method of claim 1, wherein the Ergothioneine is L-ergothioneine.

6. The method of claim 1, wherein the Ergothioneine is administered in a dose from 0.01 to 500 mg/kg body weight per day.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial
<220> FEATURE:
<223> OTHER INFORMATION: Synthetic Primer

<400> SEQUENCE: 1
gggtgtggtc cagaggact 19

<210> SEQ ID NO 2
<211> LENGTH: 20
<212> TYPE: DNA
<213> ORGANISM: Artificial
<220> FEATURE:
<223> OTHER INFORMATION: Synthetic Primer

<400> SEQUENCE: 2
tagttgccag ccatctgttg 20

<210> SEQ ID NO 3
<211> LENGTH: 20
<212> TYPE: DNA
<213> ORGANISM: Artificial
<220> FEATURE:
<223> OTHER INFORMATION: Synthetic Primer

<400> SEQUENCE: 3
gactgacata ccattgaagc 20

<210> SEQ ID NO 4
<211> LENGTH: 20
<212> TYPE: DNA
<213> ORGANISM: Artificial
<220> FEATURE:
<223> OTHER INFORMATION: Synthetic Primer

<400> SEQUENCE: 4
gcattcgcca caggctcttc 20

<210> SEQ ID NO 5
<211> LENGTH: 20
<212> TYPE: DNA
<213> ORGANISM: Artificial
<220> FEATURE:
<223> OTHER INFORMATION: Synthetic Primer

<400> SEQUENCE: 5
ctgtgttggc cagcacagac 20

<210> SEQ ID NO 6
<211> LENGTH: 20
<212> TYPE: DNA
<213> ORGANISM: Artificial
<220> FEATURE:
<223> OTHER INFORMATION: Synthetic Primer

<400> SEQUENCE: 6
cgcagcgcat cgccttctat 20